US011426548B2

(12) United States Patent
Zhou

(10) Patent No.: US 11,426,548 B2
(45) Date of Patent: Aug. 30, 2022

(54) COMBINED LARYNGEAL-BRONCHIAL LUNG SEPARATION SYSTEM

(71) Applicant: Gary Zhou, Guilford, CT (US)

(72) Inventor: Gary Zhou, Guilford, CT (US)

(*) Notice: Subject to any disclaimer, the term of this patent is extended or adjusted under 35 U.S.C. 154(b) by 299 days.

(21) Appl. No.: 16/568,980

(22) Filed: Sep. 12, 2019

(65) Prior Publication Data

US 2020/0001032 A1 Jan. 2, 2020

Related U.S. Application Data

(63) Continuation-in-part of application No. 16/177,957, filed on Nov. 1, 2018, now Pat. No. 10,441,735.

(60) Provisional application No. 62/670,418, filed on May 11, 2018.

(51) Int. Cl.
*A61M 16/04* (2006.01)

(52) U.S. Cl.
CPC .... *A61M 16/0404* (2014.02); *A61M 16/0434* (2013.01); *A61M 16/0447* (2014.02); *A61M 16/0459* (2014.02); *A61M 16/0488* (2013.01); *A61M 16/0484* (2014.02)

(58) Field of Classification Search
CPC .............. A61M 16/04; A61M 16/0404; A61M 16/0409; A61M 16/0431; A61M 16/0434; A61M 16/0475; A61M 16/0488
See application file for complete search history.

(56) References Cited

U.S. PATENT DOCUMENTS

| | | | | |
|---|---|---|---|---|
| 5,165,420 A | * | 11/1992 | Strickland | A61M 16/0486 600/581 |
| 5,241,956 A | | 9/1993 | Brain | |
| 5,305,740 A | * | 4/1994 | Kolobow | A61M 16/04 128/207.14 |

(Continued)

FOREIGN PATENT DOCUMENTS

| CN | 201823142 U | 5/2011 |
|---|---|---|
| CN | 102120056 A | 7/2011 |

(Continued)

OTHER PUBLICATIONS

International Search Report and Written Opinion from related International Patent Application No. PCT/US2020/018748 dated May 22, 2020.

(Continued)

*Primary Examiner* — Joseph D. Boecker
(74) *Attorney, Agent, or Firm* — McCarter & English, LLP

(57) ABSTRACT

The present disclosure describes systems and apparatuses related to a bronchial isolation tube, a laryngeal mask or similar device, and/or adapters and connectors for use with the same, as well as methods for using the same. In an exemplary airway device, the device may comprise a mask portion being defined at a distal end of the airway device, and may be configured and dimensioned to be positioned in a hypopharyngeal area of a patient to cover and seal around a glottis of the patient; and a channel portion extending from a proximal end of the airway device to the mask portion. The channel portion may include first and second channels, wherein the second channel may obliquely merge with the first channel proximate to an opening of the first channel. In an exemplary embodiment, a third channel may form a combined pharyngeal-gastric access channel.

16 Claims, 15 Drawing Sheets

(56) References Cited

U.S. PATENT DOCUMENTS

| | | | |
|---|---|---|---|
| 5,315,992 A * | 5/1994 | Dalton | A61M 16/04 128/207.15 |
| 6,443,156 B1 | 9/2002 | Niklason et al. | |
| 7,997,274 B2 | 8/2011 | Baska | |
| 8,757,159 B2 | 6/2014 | Nierich | |
| 9,357,905 B2 | 6/2016 | Molnar et al. | |
| 9,744,323 B2 | 8/2017 | Hoftman et al. | |
| 9,956,367 B1 | 5/2018 | Sun | |
| 2003/0040678 A1 * | 2/2003 | Robinson | A61B 5/0813 600/531 |
| 2004/0144387 A1 | 7/2004 | Amar | |
| 2007/0017527 A1 | 1/2007 | Totz | |
| 2008/0071249 A1 | 3/2008 | Vadivelu | |
| 2008/0276936 A1 | 11/2008 | Cook | |
| 2009/0000622 A1 | 1/2009 | Murray | |
| 2011/0023890 A1 | 2/2011 | Baska | |
| 2011/0220117 A1 | 9/2011 | Dubach | |
| 2012/0048279 A1 | 3/2012 | Brain | |
| 2013/0186407 A1 * | 7/2013 | Hammer | A61M 16/0484 128/207.15 |
| 2013/0220332 A1 | 8/2013 | Baska et al. | |
| 2013/0269689 A1 | 10/2013 | Brain | |
| 2013/0324798 A1 | 12/2013 | Molnar et al. | |
| 2014/0000624 A1 | 1/2014 | Miller | |
| 2014/0128672 A1 | 5/2014 | Daher et al. | |
| 2014/0150782 A1 | 6/2014 | Vazales et al. | |
| 2014/0309494 A1 | 10/2014 | Molnar | |
| 2014/0323806 A1 | 10/2014 | Brain | |
| 2015/0007826 A1 * | 1/2015 | Chaudhry | A61M 16/0434 128/207.15 |
| 2015/0122251 A1 * | 5/2015 | Azhir | A61M 16/0486 128/200.26 |
| 2015/0151063 A1 * | 6/2015 | Hoftman | A61M 16/0404 600/109 |
| 2016/0038014 A1 | 2/2016 | Molnar | |
| 2016/0114117 A1 | 4/2016 | Cook | |
| 2016/0206841 A1 | 7/2016 | Vadivelu | |
| 2016/0243326 A1 * | 8/2016 | Hammer | A61M 16/0459 |
| 2017/0216544 A1 | 8/2017 | Baska | |
| 2018/0228991 A1 | 8/2018 | Cook | |

FOREIGN PATENT DOCUMENTS

| | | |
|---|---|---|
| CN | 205215883 U | 5/2016 |
| CN | 105214188 B | 7/2017 |
| JP | 4424902 B2 | 3/2010 |
| WO | 2009025843 A1 | 2/2009 |
| WO | 2017080347 A1 | 5/2017 |

OTHER PUBLICATIONS

International Search Report and Written Opinion from related International Patent Application No. PCT/US2019/031323 dated Jun. 13, 2019.

International Search Report and Written Opinion from related International Patent Application No. PCT/US2020/050405 dated Feb. 16, 2021.

Zhou, Gary X., "Laryngeal Mask Airway Embedded With Pharyngeal Suction Catheters for Rhinoplasty: A Case Report." A A Pract. Jan. 1, 2018; 1 0(1): 13-15. doi: 1 0.1213/XAA.0000000000000622.; retrieved from https://journals.lww.com/aacr/fulltextl/2018/01010/Laryngeal_Mask_Airway_Embedded_With_Pharyngeal.4.aspx.

Supplementary European Search Report for Application No. 19799959. 2, dated Jan. 4, 2022, 9 pages.

* cited by examiner

COMBINED LARYNGEAL-BRONCHIAL LUNG SEPARATION SYSTEM

RELATED APPLICATION

This application is a continuation-in-part of U.S. patent application Ser. No. 16/177,957, filed on Nov. 1, 2018, which claims the benefit of priority to U.S. Provisional Application No. 62/670,418 filed on May 11, 2018, the disclosures of which are incorporated by reference herein in their entirety.

TECHNICAL FIELD

Aspects of the present disclosure relate to a medical apparatus that is comprised of an airway device or system. In some instances, aspects of the present disclosure relate to apparatuses capable of achieving isolation and deflation of, as well as ventilation and access to, the operative or diseased lung during surgeries and procedures requiring one-lung ventilation or one-lung anesthesia in patients with normal or difficult airways.

BACKGROUND

Lung separation with one-lung ventilation is a medical and anesthetic technique that may be employed during certain surgical operations that involve thoracotomy, thoracoscopy or video-assisted thoracoscopic surgery, as well as for medical conditions such as pulmonary alveolar protienosis. One-lung ventilation may be achieved by blocking and isolating one side of the lungs, while selectively ventilating either the ipsilateral or contralateral side of the lungs. Such a procedure may permit a collapsed lung to facilitate the surgical operation and, more importantly, prevent contamination to the contralateral healthy lung from blood or pus materials. In one such method, one-lung ventilation may be achieved by including a single-lumen endobronchial tube, a double lumen endotracheal tube (or double lumen tube, DLT), and a bronchial blocker in conjunction with an endotracheal tube.

The conventional single-lumen endobronchial tube may be placed or configured in one of the main bronchi to block and ventilate the ipsilateral healthy or non-operative lung. This tube may be simple in structure and may be easy to place but may have disadvantages. Some disadvantages may include: 1) because the right main bronchus is short and close to the tracheal bifurcation, when a single-lumen endobronchial tube is placed in the right side, its cuff may block the takeoff of the right upper lobe bronchus, restricting ventilation only to the right middle and lower lobes, a condition usually unsuitable for effective ventilation and oxygenation; 2) this type of tube may not deflate nor provide access to the contralateral diseased or operative lung; and 3) if inflation or ventilation of the contralateral operative lung is needed for surgical or anesthetic reasons during lung operation, the tube may be retracted to the trachea, thereby compromising the isolation and leading to contamination. As a result, the conventional single-lumen endobronchial tube has generally become obsolete in practice, with the exception of occasional use in small children when no other methods can be used.

The conventional double-lumen (endotracheal or endobronchial) tube (DLT) is essentially an endobronchial tube bound to an endotracheal tube. When in place, the endobronchial tube fits in the main bronchus, isolating and ventilating one side of the lungs, while the endotracheal part resides in the trachea and provides access and ventilation to the other side. Therefore, when placed correctly, the DLT provides isolation of, as well as access and ventilation to, both sides of the lungs. This is especially advantageous in certain clinical conditions such as severe pulmonary protienosis requiring lavage, unilateral pulmonary abscess or hemorrhage, or bronchial fistula in which separation of lungs are absolutely necessary. Two major drawbacks DLTs are related to the bulkiness of the construction of the DLT. The drawbacks can include: (1) severe injury to airway may occur, and (2) it can be a challenge to place a DLT n difficult airway scenarios such as difficult laryngoscopy or intubation, lesions and abnormal anatomy of the trachea, or when nasal intubation may be required. Furthermore, if postoperative intubation is indicated, the DLT must be removed and the patient must be reintubated with a regular endotracheal tube after the surgery when airway conditions are generally compromised due to the intubation.

To overcome the aforementioned disadvantages of the DLT, bronchial blockers were introduced for use with the regular endotracheal tubes. These bronchial blockers can be placed either alongside or inside the endotracheal tube, and include the original Uninvent tube and subsequent Uni-blocker (Fuji), Arndt, Cohen, Coopdech endobronchial blockers, EZ-blocker, and other balloon-tipped catheters. While each of the foregoing structures has unique properties, all may include a distal cuff to block a main or lobar bronchus of the ipsilateral operative lung, and most have a small lumen (<2 mm) for evacuation and collapse of, as well as for continuous positive airway pressure (CPAP) application to, the operative lung. The bronchial blocker technique offers several benefits over the DLT. The endotracheal tube associated with this technique may be generally easy to place and may be successful in difficult airways requiring techniques not suitable for the DLT. During a combined thoracotomy and laparotomy procedure, the blocker may be removed after finishing the thoracotomy, leaving only the endotracheal tube for the abdominal procedure. Similarly, the endotracheal tube may be left for postoperative ventilation if required, thereby avoiding postoperative tracheal tube exchange.

Although the comparative efficacy and complication rates of the DLT versus the bronchial blockers are debatable, one significant shortcoming associated with a conventional bronchial blocker is that the evacuation of secretions, blood or pus from the operative or diseased lung is neither effective nor reliable through its small lumen (2 mm or less), which clogs easily and becomes inoperable, and even leads to reinflation of the operative lung. In addition, placing a large endotracheal tube for housing a conventional bronchial blocker is still challenging if possible in patients with difficult intubation. Finally, and more importantly, conventional bronchial blockers typically do not provide working access or ventilation to the blocked lung, and, therefore, cannot generally be used for bronchial lavage, pulmonary hemorrhage, bronchopleural fistula or bronchial surgery during which access to the diseased lung is critical.

Laryngeal mask airway and other supraglottic airway devices may serve as alternatives to mask ventilation and tracheal intubation, or as rescue airways and conduits for tracheal intubation. When placed properly, the laryngeal mask may cover the larynx with its tip resting on the upper end of the esophagus and its airway lumen facing the glottic opening. Generally, the laryngeal mask may create a seal around the glottis, forming a functional connection between its airway lumen and the trachea. The second generation of laryngeal mask airways includes a gastric access channel that may passively drain or actively evacuate gastric contents, and may vent air leakage from the airway, allowing for higher intra-airway pressure during positive ventilation. Practitioners have often relied on the laryngeal mask airway and other similar devices for airway management in a variety of surgeries including functional craniotomies, bronchoscopy, laparoscopy procedures; however, their application in thoracic surgery has been limited, and involves the laryngeal mask in combination with a bronchial blocker. The combination of a laryngeal mask and a bronchial blocker offers a new alternative method of one-lung ventilation, particularly in difficult airway; however, it cannot avoid the limitations of the bronchial blockers, namely limited efficacy and lack of access to the diseased lung.

SUMMARY

Aspects of the present disclosure, and according to exemplary embodiments taught herein, relate to airway devices, systems, and associated methods. Exemplary embodiments of the present disclosure can facilitate lung separation and one-lung ventilation for surgeries involving the thorax and for certain pulmonary medical conditions.

In accordance with embodiment of the present disclosure, an airway device is disclosed that includes a mask portion and a channel portion. The mask portion is defined as a distal end of the airway device. The channel portion extends from a proximal end of the airway device to the mask portion. The channel portion includes first and second channels, where the first channel extends from a first opening formed at the proximal end to a second opening formed at the mask portion. The second channel includes a first opening of the second channel formed at the proximal end. The second channel extends in the channel portion towards the mask portion and obliquely merging with the first channel in the channel portion.

In accordance with embodiments of the present disclosure, an airway device is disclosed. The airway device includes a mask, an airway channel, and a pharyngeal-gastric access channel. The mask includes an ampulla and at least one sump in fluid communication with the ampulla. The airway channel extends from a first opening of the airway channel to a second opening formed in the mask. The pharyngeal-gastric access channel extends from a first opening of the pharyngeal-gastric access channel to the ampulla in the mask portion. The ampulla includes a first port at which the pharyngeal-gastric access channel terminates and through which the pharyngeal-gastric access channel and ampulla are in fluid communication, a second port opposingly spaced from the first port, and a third port operatively at which the at least one sump terminate and through which the at least one sump and the ampulla are in fluid communication.

In accordance with embodiments of the present disclosure, an exemplary airway device is disclosed. The airway device may comprise a mask portion being defined at a distal end of the airway device. The mask portion may be configured and dimensioned to be positioned in a hypopharyngeal area of a patient to cover and seal around a glottis of the patient. The airway device may further comprise a channel portion extending from a proximal end of the airway device to the mask portion. The channel portion may include first and second channels, wherein the first channel (e.g., an airway channel) may extend from a (first) opening of the first channel formed at the proximal end to a (second) opening of the first channel formed at the mask portion, and the second channel (e.g., an imaging channel) may extend from a (first) opening of the second channel formed at the proximal end and alongside the first channel. The second channel may obliquely merge with the first channel proximate to the second opening of the first channel.

In an example embodiment, the second channel may obliquely merge with the first channel at an angle of about three to about ten degrees relative to the first channel and/or the first channel may include a groove formed in a side wall of the first channel proximate to the second opening, and a (second) opening of the second channel may obliquely merge with the first channel at the groove. The groove may taper radially inward with respect to the first channel from the second opening of the second channel to the second opening of the first channel. The second channel may include a visual indicator that may extend along at least a portion of a length of the second channel.

The mask portion may further include an ampulla and at least one sump. The at least one sump may be formed in the mask portion and may be in fluid communication with the ampulla through a first port of the ampulla. The ampulla may be embedded in the mask portion. The at least one sump may be formed as a recess in the mask portion that may extend along a portion of the perimeter of the mask portion. A size of the recess may increase from a first end of the recess to a second end of the recess, wherein the second end of the recess may be in fluid communication with the first port of the ampulla. The mask portion may further include a second sump formed therein, wherein the second sump may be in fluid communication with the ampulla through a second port of the ampulla. The ampulla may further include a third port that may open towards an esophagus of the patient when the mask portion is positioned in a hypopharyngeal area of a patient to cover and seal around a glottis of the patient.

The channel portion may include a third channel that may extend alongside the first channel and/or second channel from the proximal end to the ampulla. A first opening of the third channel can be formed the proximal end. The third channel may be in fluid communication with the first, second, and third ports of the ampulla. The first, second, and/or third channels may further include tubular inner side walls, wherein the first channel may have a diameter that is greater than the second channel and/or third channel.

In accordance with embodiments of the present disclosure, an exemplary airway device is disclosed. The exemplary airway device may comprise a mask portion. The mask portion may comprise at least one sump that may be formed in the mask portion along a portion of the perimeter of the mask portion; and an ampulla including a plurality of ports. A first one of the plurality of ports may terminate as an opening in the mask portion. A second one of the ports may be in fluid communication with the at least one sump.

A channel portion may extend from a proximal end of the airway device to the mask portion, and may include first and second channels. The first channel (e.g., an airway channel) may extend from a (first) opening of the first channel formed at the proximal end to a (second) opening of the first channel formed in the mask portion. The second channel (e.g., a combined pharyngeal-gastric access channel) may extend from a (first) opening of the second channel formed at the proximal end and alongside the first channel to the mask portion, wherein the second channel may terminate as the ampulla. The second channel may be in fluid communication with the at least one sump via the first one of the plurality of ports and may be in fluid communication with the second one of the plurality of ports.

In an exemplary embodiment, the ampulla may be embedded in the mask portion. The at least one sump may be formed as a recess in the mask portion that may extend along a portion of the perimeter of the mask portion. A size of the recess may increase from a first end of the recess to a second end of the recess. The second end of the recess may be in fluid communication with the first one of the plurality of ports of the ampulla. The mask portion may also include a second sump formed in the mask portion. The second sump may be in fluid communication with the ampulla through a third one of the plurality of ports of the ampulla. The channel portion may comprise a third channel (e.g., an imaging channel) that may obliquely merge with the first channel, for example, at an angle of about three to about ten degrees relative to the first channel. The first, second, and third channels may include tubular inner side walls, and the first channel may have a diameter that is greater than the second and third channels. A portion of the second channel may curve along the mask portion towards a midline of the mask portion.

In accordance with embodiments of the present disclosure, a bronchial isolation tube is disclosed. The bronchial isolation tube includes an elongated tubular body that extends from a proximal end to a distal end. The elongated tubular body is configured and dimensioned to be inserted into an upper airway of a human, and to be passed through a trachea and into a bronchus of the human. A first port is disposed at the proximal end of the elongated tubular body and a distal opening disposed at the distal end of the elongated tubular body. The elongated tubular body has a portion with a reduced diameter compared to a remainder of the elongated tubular body. The portion with the reduced diameter is positioned across a glottis of the human when the distal end of the elongated tubular body is positioned in the bronchus of the human. The elongated tubular body can have a uniform thickness and can include an upper section, a middle section, a lower section, and a distal section, where the middle section is disposed between the upper and lower sections and can correspond to the portion of the elongated tubular body with the reduced diameter. The reduced diameter of the middle portion can be approximately ten percent to approximately twenty percent and/or approximately a half millimeter to approximately one and a half millimeters smaller than the diameter of the remainder of the elongated tubular body.

The elongated tubular body can have a length measured along a central axis of the elongated tubular body from the proximal end to the distal end. The middle section can correspond to ten percent to twenty percent of the length of the elongated tubular body; the middle section can begin approximately two-hundred ten millimeters to approximately two-hundred fifty millimeters from the proximal end of the elongated tubular body; the middle section can end approximately two-hundred sixty millimeters to approximately three hundred millimeter from the proximal end of the elongated tubular body; the upper section can be four to six times longer than the middle section; the lower section can be approximately two to three times longer than the middle section; and/or the middle section can have a length of approximately 40 millimeters to approximately 60 millimeters.

The distal section can include an inflatable member (e.g., a cuff or balloon) disposed on the elongated tubular body in proximity to the distal end and can include a Murphy eye disposed in the elongated tubular body proximate to the distal end. The elongated tubular body can extend linearly from the proximal end towards the distal section, and the distal section can be biased so that the distal section extends at an angle relative to a remainder of the elongated tubular body. The distal section of the elongated tubular body can extend at an angle of approximately twenty-five degrees to approximately thirty-five degrees relative to the upper, middle, and lower sections of the elongated tubular body or can extend at an angle of approximately forty to approximately fifty degrees relative to the upper, middle, and lower sections of the elongated tubular body. In some embodiments, the distal section can extend at an angle of zero or nearly zero relative to the upper, middle, and lower sections of the elongated tubular body.

The inflatable member can be formed symmetrically or asymmetrically about the elongated tubular body. For embodiments in which the inflatable member is formed asymmetrically about the elongated tubular body, the inflatable member can include a short axis that extends between the Murphy eye and a visual indicator disposed proximally on the elongated tubular body relative to the Murphy eye and can include a long axis that extends between the visual indicator and the distal opening without covering the Murphy eye.

In accordance with embodiments of the present disclosure, a three-way connecting tube is disclosed. A proximal end of the three-way connecting tube is configured and dimensioned to couple to an anesthesia circuit. The three-way connecting tube can include a first branch and a second branch. The first branch can be configured and dimensioned to be connected to an airway channel of a laryngeal mask. The second branch can be configured and dimensioned to be connected to a bronchial isolation tube. The first branch can include a pressure relief valve to limit a pressure to the laryngeal mask while ensuring a higher pressure to a bronchial isolation tube. The three-way connecting tube can include a built-in thermo-moisture filter and a $CO_2$ sampling port.

In accordance with embodiments of the present disclosure, an exemplary system is disclosed. The system may comprise a laryngeal mask and a bronchial isolation tube. The laryngeal mask may comprise a mask portion formed at a distal end of the laryngeal mask. The mask portion may be configured and dimensioned to be positioned in a hypopharyngeal area of a patient to cover and seal around a glottis of the patient. The laryngeal mask can include a channel portion that may extend from a proximal end of the laryngeal mask to the mask portion. The channel portion may include a plurality of channels to facilitate fluid communication between the proximal and distal ends of the laryngeal mask. The channels may include (i) an airway channel that may extend from a first opening of the airway channel formed at the proximal end to a second opening of the airway channel formed at the mask portion, and (ii) an imaging channel that may extend from a first opening of the imaging channel formed at the proximal end. The imaging channel may extend alongside the airway channel and may obliquely merge with the airway channel proximate to the second opening of the airway channel.

The bronchial isolation tube may be configured and dimensioned to be inserted into the first opening of the airway channel and through the second opening of the airway channel, passed a trachea and into a left or right bronchus of the patient, when the mask portion is positioned in the hypopharyngeal area of the patient. An inflatable member may be disposed on the bronchial isolation tube proximate to a bronchus distal end. The inflatable member may be configured to isolate the left or right bronchus. The bronchus distal end of the bronchial isolation tube may include a murphy eye and a visual indicator. The visual indicator may be disposed on the bronchial isolation tube at a distance of approximately five millimeters proximally away from the inflatable member towards an input proximal end of the bronchial isolation tube. The bronchus distal end of the bronchial isolation tube may have a slight curve to bias the bronchus distal end towards the left or right bronchus when the bronchus distal end is inserted into the left or right bronchus. The bronchial isolation tube may terminate with a Y-shaped structure at an input proximal end of the bronchial isolation tube.

In accordance with embodiments of the present disclosure, the system may further comprise a multiport adapter configured to mate with the proximal end of the laryngeal mask to facilitate mounting of the bronchial isolation tube to the laryngeal mask and to facilitate ventilating of the patient when the mask portion is positioned in the hypopharyngeal area of the patient to cover and seal around a glottis of the patient. A dual clamp system defined as a large clamp to hold under the top edge of an adapter or a laryngeal mask and a smaller clamp to hold the bronchial isolation tube or a tracheal tube may join the multiport adaptor or the laryngeal mask and the bronchial isolation tube or a tracheal tube together when the bronchial isolation tube or a tracheal tube is inserted through the adapter and/or the laryngeal mask into a patient airway.

In accordance with embodiments of the present disclosure, the imaging channel may be configured and dimensioned to receive an imaging device, and the imaging channel may merge with the airway channel at an angle that facilitates imaging of the glottis. The imaging channel may be configured and dimensioned to receive an imaging device, and the imaging channel may merge with the airway channel at an angle that facilitates side-by-side insertion of the bronchial isolation tube and the imaging device to facilitate imaging of the main bronchus to ensure that a bronchus is unobstructed by the inflatable member of the bronchial isolation tube when the bronchus distal end is positioned in left or right bronchus.

In accordance with embodiments of the present disclosure, the mask portion may include an ampulla, and the plurality of channels of the channel portion may include a combined pharyngeal-gastric access channel that may extend from the proximal end of the laryngeal mask to the ampulla. A first opening of the combined pharyngeal-gastric access channel can be formed at the proximal end. The mask portion may further include first and second sumps formed in the back of the mask portion. The first sump may be in fluid communication with the ampulla via a first port of the ampulla, and the second sump may be in fluid communication with the ampulla via a second port of the ampulla. The ampulla may include a third port that may open towards an esophagus of the patient when the mask portion is positioned in the hypopharyngeal area of the patient to cover and seal around a glottis of the patient.

In accordance with embodiments of the present disclosure, the combined pharyngeal-gastric access channel may be in fluid communication with the first, second, and third ports of the ampulla. A gastric suction tube may be configured to be inserted into a stomach of the patient via the combined pharyngeal-gastric access channel, the ampulla, and the third port of the ampulla to remove gastric fluids from the stomach. The gastric suction tube may be configured to be inserted into the ampulla via the combined pharyngeal-gastric access channel to remove pharyngeal fluid from the first and second sumps.

In accordance with embodiments of the present disclosure, the airway channel may also include a groove formed in a side wall of the airway channel proximate to the second opening of the airway channel, and the imaging channel may obliquely merge with the first channel at the groove. The groove may taper radially inward with respect to the airway channel as the imaging channel merges with the airway channel. The imaging channel may include a visual indicator that may extend along at least a portion of a length of the imaging channel. The imaging channel may obliquely merge with the airway channel at an angle of about three to about ten degrees relative to the airway channel.

In accordance with embodiments of the present disclosure, an exemplary method of forming an airway device is disclosed. The method of forming the airway device may include the following steps: forming a mask portion at a distal end of the airway device and forming a channel portion that extends from the mask portion. The mask portion may be configured and dimensioned to be positioned in a hypopharyngeal area of a patient to cover and seal around a glottis of the patient. The channel portion that may extend from a proximal end of the airway device to the mask portion, wherein forming the channel portion can include: defining a first channel to extend from a first opening of the first channel formed at the proximal end to a second opening of the first channel formed at the mask portion; defining a second channel to extend from a first opening of the second channel formed at the proximal end; and defining the second channel to extend alongside the first channel and to obliquely merge with the first channel proximate to the second opening of the first channel.

The method may further include defining a groove formed in a side wall of the first channel proximate to the second opening of the first channel where the second channel obliquely merges with the first channel. The groove may taper radially inward with respect to the first channel as the second channel merges with the first channel. The mask portion may further include an ampulla and at least one sump in the mask portion. The at least one sump may be in fluid communication with the ampulla through a first port of the ampulla. The ampulla may be embedded in the mask portion. The at least one sump may be formed as a recess in the mask portion that may extend along a portion of the perimeter of the mask portion. The ampulla may include a second port that may be configured to open to an esophagus of the patient when the mask portion is positioned in hypopharyngeal area of a patient to cover and seal around a glottis of the patient. The method may further comprise defining a third channel that extends alongside the first and second channels from the proximal end to the ampulla. A first opening of the third channel can be formed at the proximal end. The third channel can be in fluid communication with the first and second ports of the ampulla.

In accordance with embodiments of the present disclosure, an exemplary bronchial isolation tube is described. In an exemplary embodiment, the bronchial isolation tube may comprise a first elongated tube portion that may extend generally linear from a proximal end to a first transition area; and a second elongated tube portion that may extend from the first transition area to a distal end of the bronchial isolation tube at an angle relative to the first elongated tube portion. The second elongated tube portion of the left-sided bronchial isolation tube can have a curvature formed therein. An inflatable member may be disposed proximate to the distal end; and a murphy eye may be formed in the second elongated tube portion between the inflatable member and the distal end. The bronchial isolation tube may further comprise a y-shaped structure at the proximal end and include a first and second port. The bronchial isolation tube may be configured as a left-sided bronchial isolation tube for insertion into the left bronchus. The second elongated tube portion may have a length of about 40 to about 50 millimeters, and/or the inflatable member may have a generally spherical shape. The bronchial isolation tube may also be configured as a right-sided bronchial isolation tube for insertion into the right bronchus, in which the second elongated tube portion may have a length of about 25 to about 35 millimeters, and/or the inflatable member may be disposed to surround but not to obstruct the murphy eye when the inflatable member is inflated. The bronchial isolation tube may further comprise a steering assembly to adjust the angle at which the second elongated tube portion extends relative to the first elongated tube portion. The steering assembly may include a wire disposed along the first and second elongated tube portions and a steering member may be disposed at the proximal end of the bronchial isolation tube. The steering member may be operatively coupled to the wire and configured to manipulate the wire to adjust the angle at which the second elongated tube portion extends relative to the first elongated tube portion.

In accordance with embodiments of the present disclosure, one or more kits are disclosed. The kit can include a laryngeal mask, a bronchial isolation tube, a gastric suction tube, and/or an imaging tube.

Other objects and features will become apparent from the following detailed description considered in conjunction with the accompanying drawings. It is to be understood, however, that the drawings are designed as an illustration only and not as a definition of the limits of the invention.

BRIEF DESCRIPTION OF THE DRAWINGS

The accompanying drawings, which are incorporated in and constitute a part of this specification, illustrate exemplary embodiments of the present disclosure and together with the description, serve to explain the principles of the disclosure.

DETAILED DESCRIPTION

The drawings and description are not restrictive but rather illustrative in nature, with the scope of the application indicated in the claims. While this embodiment is typical and preferred, the invention is not restricted to the descriptions.

Figure 1A:
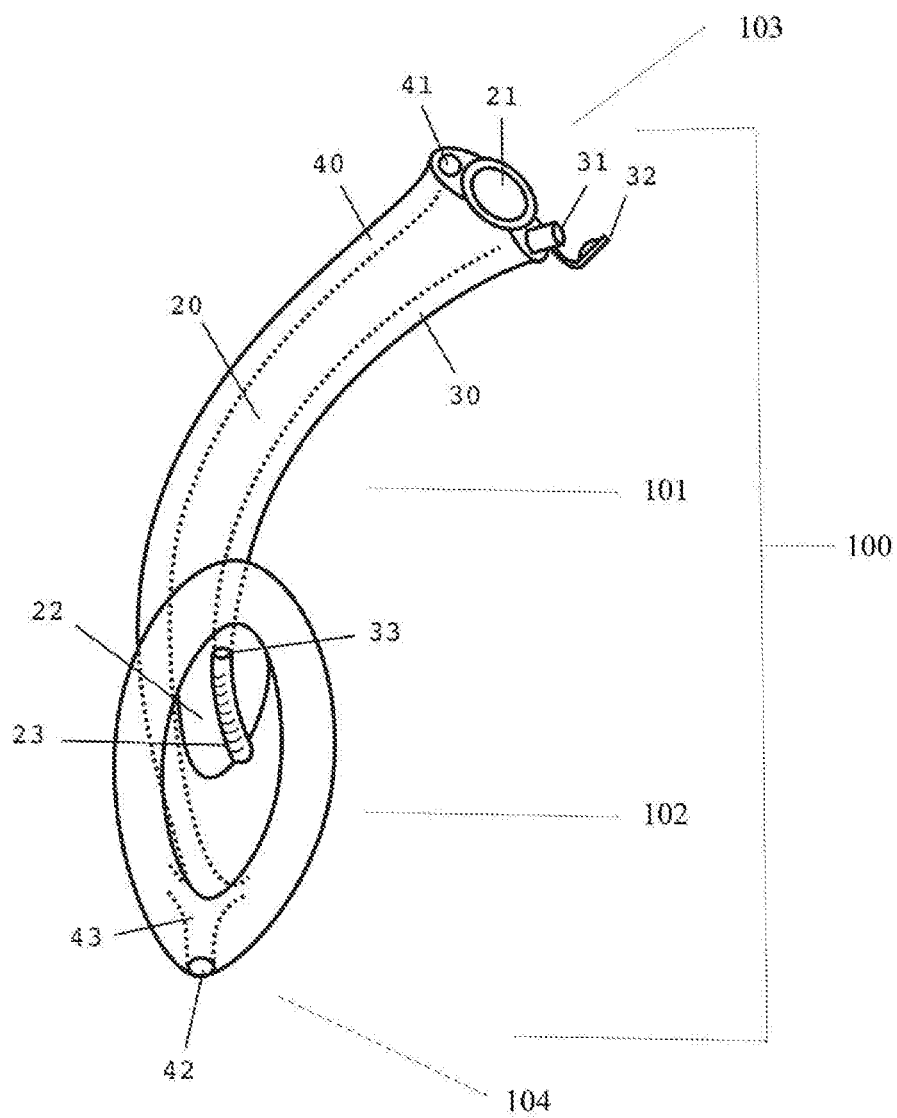
FIG. 1A illustrates a perspective view of an exemplary multi-channel laryngeal mask according to aspects of the present disclosure, and illustrates a right anterior view showing the mask, a tubular structure with a central airway channel and its distal airway lumen, an imaging channel and its proximal end and distal opening, a pharyngeal-gastric access channel and its ampulla and an esophageal opening.
Figure 1B:
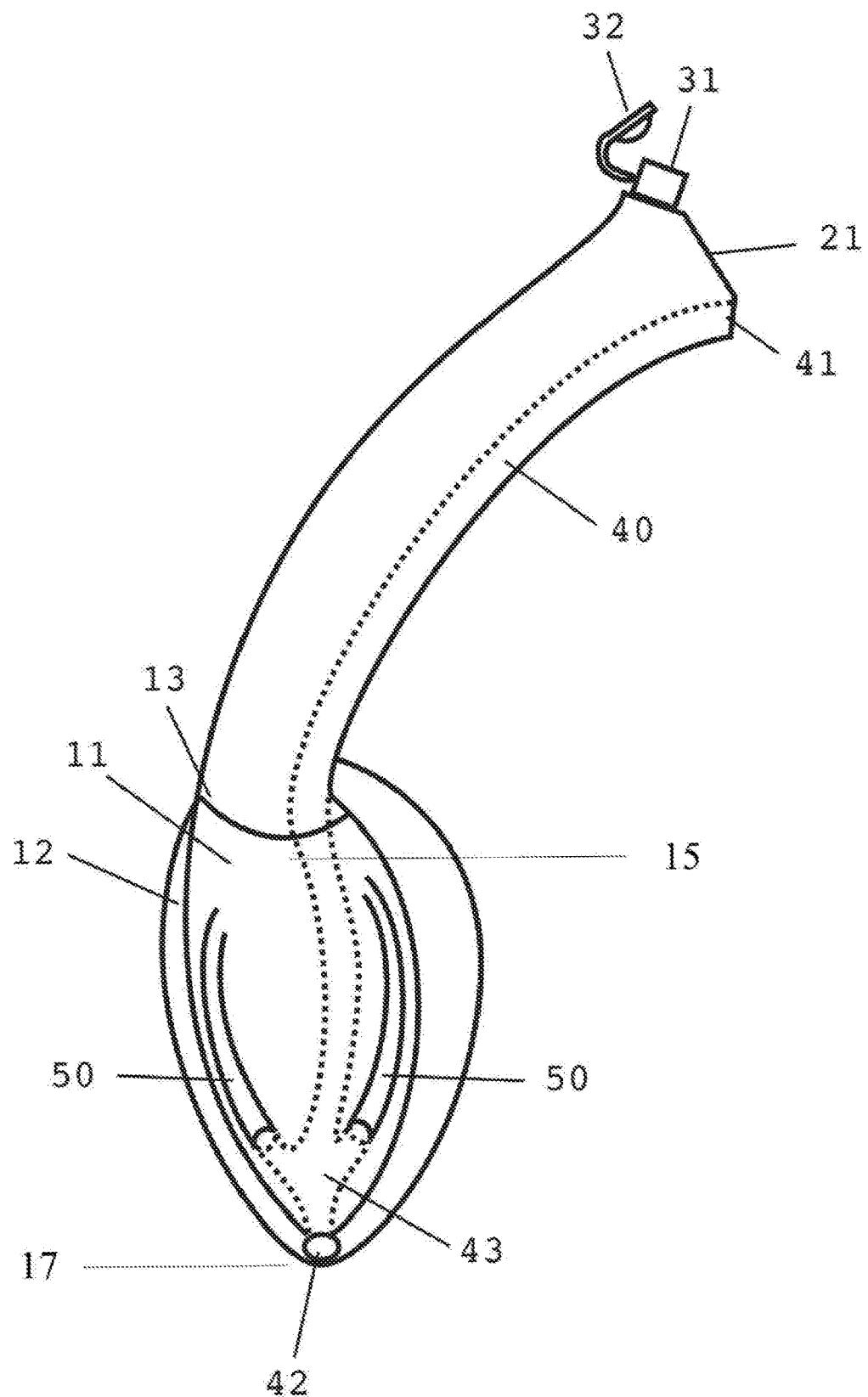
FIG. 1B illustrates a perspective view of the exemplary multi-channel laryngeal mask of FIG. 1A, and further illustrates a right posterior view showing a back of the mask with two pharyngeal sump channels or grooves that enter the ampulla, and the pharyngeal-gastric access channel, the proximal end of the imaging channel and its cap.

FIGS. 1A and 1B depict an airway device 100 in accordance with embodiment of the present disclosure. The airway device 100 can be a multi-channel laryngeal mask that can include a mask portion 102 and a channel portion 101. The channel portion 101 can extend from a proximal end 103 of the airway device 100 to the mask portion 102 at a distal end 104 of the airway device 100. The airway device 100 can be made with disposable materials, such as PVC or silicon, in different sizes to fit larger or smaller persons.

Figure 2:
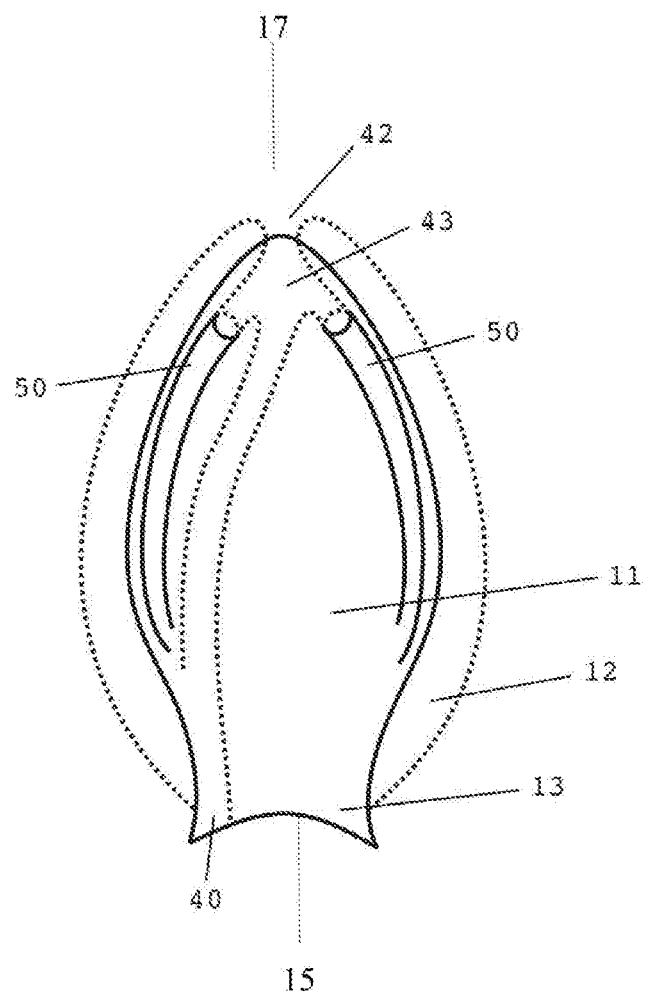
FIG. 2 illustrates a perspective view of a vaulted back and a membrane cuff of the mask of FIGS. 1A-1B with the pharyngeal-gastric access channel and its ampulla, the pharyngeal sump channels or grooves or recesses, which start at the top and follow the edge of the back plate before entering the ampulla.

The mask portion 102, as depicted in FIGS. 1B and 2, is formed by a pear-shaped vaulted back plate 11 that can be surrounded by a membrane cuff 12. The back plate 11 can have a dome shape and can have an angulated and elongated opening 13 at a top 15. The back plate 11 can be made of material firm enough to maintain the shape of the dome and the angle of the opening. The cuff 12 can be inflated either through tubing, or automatically through the airway channel during positive pressure ventilation. The mask portion 102 covers and seals around the glottis when placed properly in the hypopharyngeal area.

As shown in FIG. 1A, the channel portion 101 can engage and/or be integrally formed with the vaulted back plate 11 such that the channel portion 101 terminates at the back plate 11 of the mask portion 102. The channel portion 101 can include an airway channel 20, an imaging channel 30, and a combined pharyngeal-gastric access channel 40. The airway channel 20, the imaging channel 30, and the combined pharyngeal-gastric access channel 40 can each be lumens with tubular inner sidewalls and include openings at the proximal end 103 of the channel portion, which can form inlets to the airway device 100. For example, the airway channel 20, the imaging channel 30, and the combined pharyngeal-gastric access channel 40 can have corresponding inlet openings 21, 31, and 41, respectively (e.g., first openings). The channels 20, 30, and 40 can extend from the proximal end 103 of the airway device 100 to the back plate 11 of the mask portion 102 as described herein. The channels 20, 30, and 40 can each include openings near the distal end 104 of the airway device 100, which can form outlets from the airway device 100. For example, the airway channel 20, the imaging channel 30, and the combined pharyngeal-gastric access channel 40 can have corresponding outlet openings 22, 33, and 42, respectively (e.g., second openings).

Referring again to FIGS. 1B and 2, the vaulted back plate 11 of the mask portion 102 encloses two pharyngeal sump channels 50, which originate at the top of the back plate 11 of the mask portion 102 as two small and shallow grooves or recesses on the side walls of elongated opening 13 and extend along a perimeter of the back plate 11 of the mask, close to the edges of the mask or inward of the cuff 12 if a cuff is used. The pharyngeal sump channels 50 gradually become larger in width and depth along the edge of the back plate from the top 15 towards an apex 17 of the mask portion 102 to finally drain into the combined pharyngeal-gastric access channel 40 at an ampulla 43 of the combined pharyngeal-gastric access channel 40 near the apex 17 of the mask portion 102. The high origination provides air entry to the pharyngeal sump channel—ampulla system during suction through the combined pharyngeal-gastric channel 40 as described herein, thereby preventing vacuum injury to the pharyngeal mucosa. The ampulla 43 can be embedded and/or formed in or on the back plate 11 of the mask portion 102. The ampulla 43 can be an enclosed chamber or cavity accessible via ports which can form openings to the interior volume of the ampulla. The ampulla 43 can have a generally bulbous or spherical internal volume.

Figure 10:
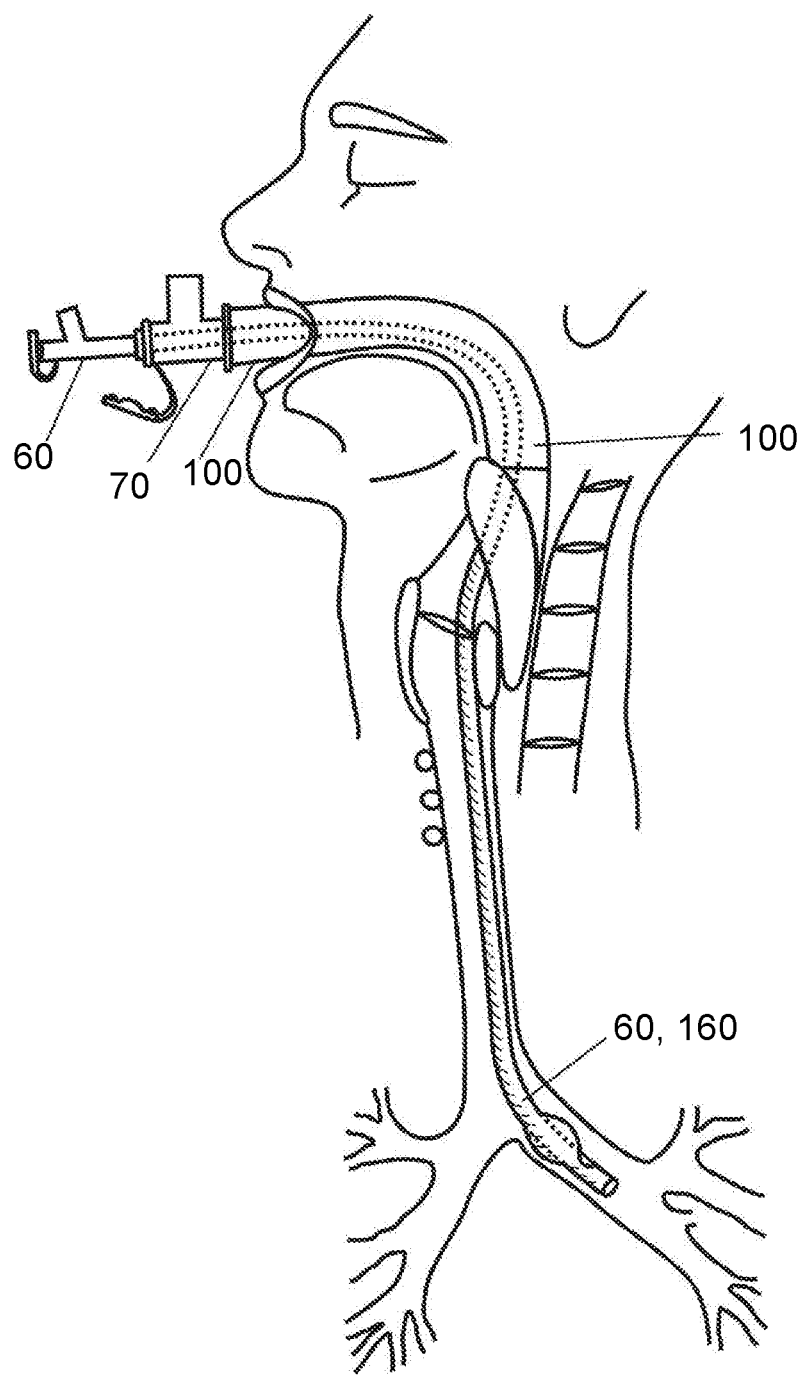
FIG. 10 illustrates a perspective view depicting an exemplary three-channel laryngeal mask according to aspects of the present disclosure described herein, the mask is shown placed in the upper airway with a bronchial isolation tube placed into the left main bronchus through a swivel adaptor attached to the laryngeal mask.

The airway channel 20 can form a main channel of the channel portion 101 and can be disposed in the center of the channel portion 101. The airway channel can allow for ventilation and passage of a tracheal or bronchial tube into a trachea of a patient when the mask portion 102 is positioned in a hypopharyngeal area of a patient to cover and seal around a glottis of the patient. The airway channel 20 is connected or integrally formed distally (FIG. 1) to the angulated opening 13 at the top 15 of the mask portion 102, and extends proximally outside the mouth when the mask portion is positioned in a hypopharyngeal area of a patient to cover and seal around a glottis of the patient. The airway channel 20 can end in a swivel adaptor, which can connect the airway device 100 to the ventilator circuit while providing access to the BIT. When the airway device 100 is placed correctly in the upper airway, the airway channel 20 aligns with the glottis and communicates with the trachea through the glottic opening sealed by the mask (FIG. 10). A diameter of the airway channel 20 can be defined to be large enough for passage of a regular tracheal tube appropriate for the size of the patient—e.g., generally a 7 to 7.5 millimeters (mm) tracheal tube for an adult of regular body frame.

Figure 3:
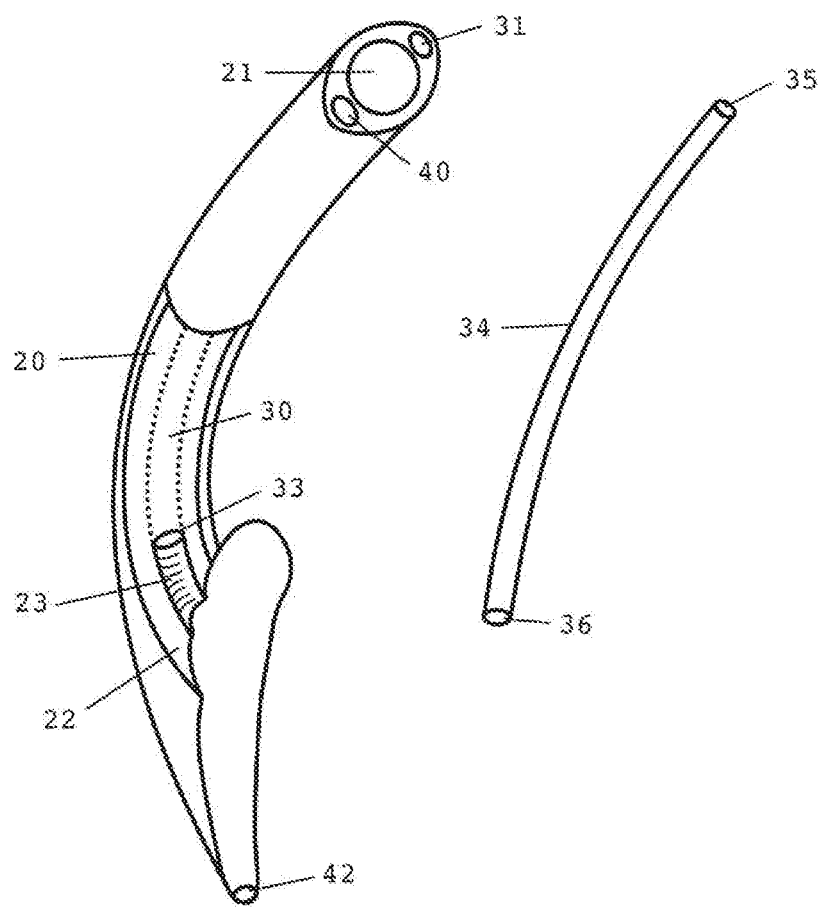
FIG. 3 Illustrates a perspective sagittal view of the laryngeal mask of FIGS. 1A-2 showing the airway channel and the imaging channel groove on its distal sidewall, and its relation to the imaging channel and the pharyngeal-gastric access channel, and a removable inner tube that has an open proximal end, and a closed and transparent distal end, that may be placed and slid in to the imaging channel.
Figure 4:
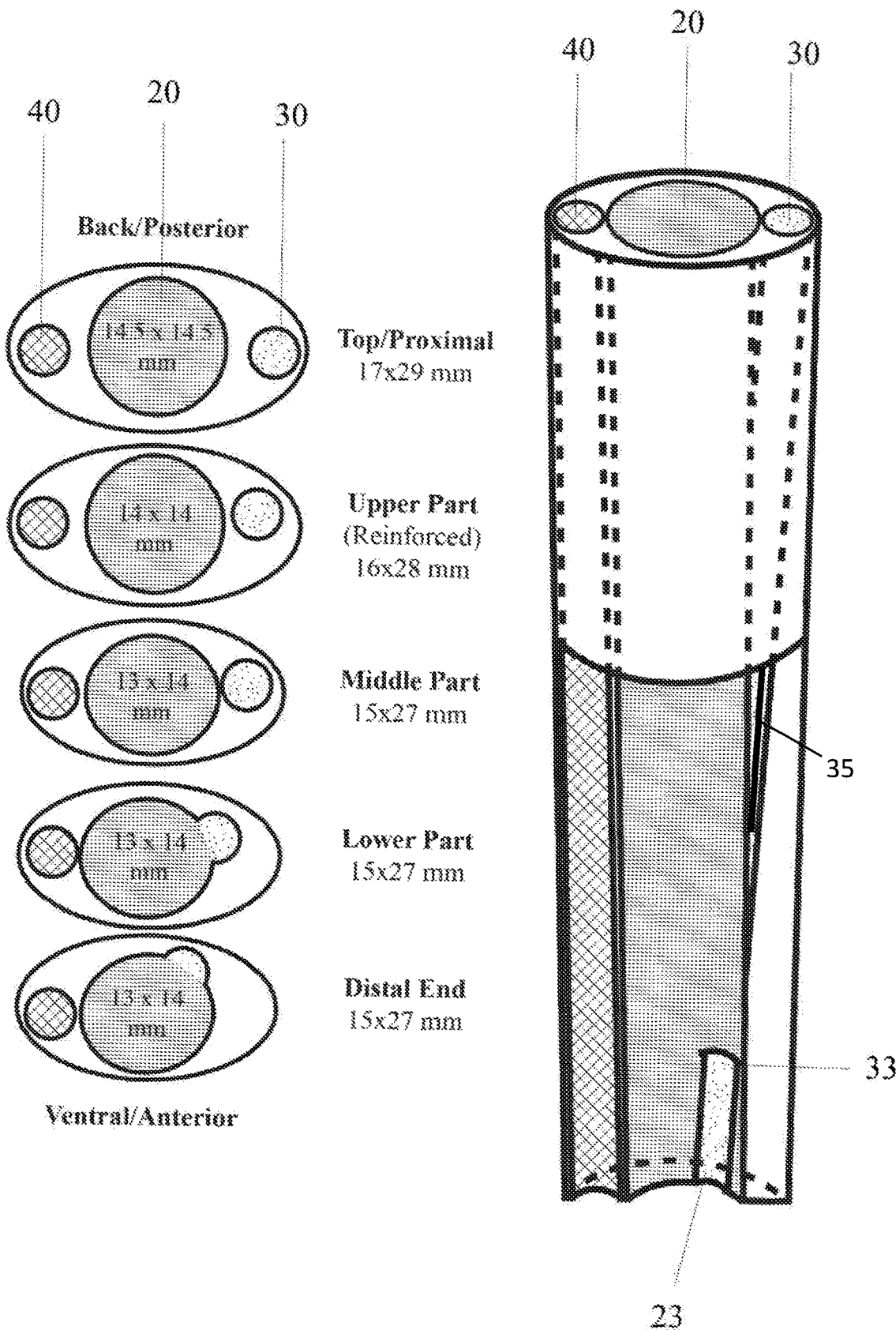
FIG. 4 illustrates a perspective sectional view of an exemplary three-channel tube according to aspects described in the present disclosure and illustrate the relationship of the central airway channel and its distal groove, the imaging channel, and the pharyngeal-gastric access channel inside the tubular structure, and further depicts the imaging channel distal end merging with the airway channel and becoming the imaging groove.

The imaging channel 30 lies on a left side of the airway channel 20, as shown in FIGS. 1A, 3 and 4. The imaging channel 30 travels alongside the airway channel 20 posteriorly and obliquely, gradually merging into the airway channel 20 at or near the 1 o'clock position (FIG. 4) at an angle of approximately of about three to about ten degrees relative to the airway channel 20, proximate to or at the joint of the airway channel 20 and the mask (e.g., at or proximate to the opening 13). Proximally, the imaging channel 30 ends with a seal ring 31 and a cap 32, which may prevent air leak through the imaging channel 30 during ventilation. The imaging channel 30 has several advantageous features when, or as, the mask portion is positioned in a hypopharyngeal area of a patient to cover and seal around a glottis of the patient. First, the open-ended design facilitates the passage of an imaging device that can provide a close-up view of the glottis from inside an airway lumen of the airway channel 20 without increasing the thickness of the airway device 100. Secondly, to improve visualization of the glottis from the imaging channel 30, an imaging groove 23 can be carved on the sidewall of the airway channel (FIGS. 3 and 4) just beyond a distal opening 33 of the imaging channel 30. Thirdly, a flexible bronchoscope or similar imaging device can be directly placed in the imaging channel 30 to visualize the glottic area and confirm the position of the mask portion 102, and to guide the passage of the tracheal tube through the vocal cords without interrupting the ventilation through the airway channel. Alternatively, the imaging device can be inserted in a removable inner tube 34 shown in FIG. 3, which can be placed in, and advanced through, the imaging channel 30. The inner tube 34 can have a closed and transparent distal end 36, which can protect the imaging device from direct contact with the patient or any bodily fluid when the imaging device is inserted into the removable inner tube 34 and advanced into the imaging channel 30 and the airway channel 20. Fourthly, the imaging channel 30 is marked with a visual indicator 35, such as colored line, to guide the advancement of the imaging device along the imagining channel 30. Following the colored line to its end, the imaging device reaches at the distal opening 33 of the imaging channel 30, providing a telescopic view of the glottis; if the imagining device is to be advanced further beyond the distal opening 33 of the imaging channel 30 and entering the airway channel 20, then the imaging device is directed through the slope of the groove 23 of the airway channel 20 which tapers radially inward with respect to the airway channel 20 such that the imaging device enters the airway channel 20 obliquely, where the imaging device gradually approaches the glottis near the midline position, providing a close-up view of the glottis. The imaging device can be left in place to monitor the dynamics of the glottis and the position of the mask portion 102 during the course of an operation without interfering with ventilation through the airway lumen of the airway channel 20. Finally, the open-ended imaging channel 30 may allow the flexible bronchoscope to pass through the vocal cords and therefore to facilitate guiding the placement of a bronchial isolation tube (BIT) (which may also be referred to as a bronchial blocking tube (BBT)) described herein through the trachea and into the target bronchus, which is essential for complete lung separation.

Referring to FIGS. 1, 2 and 4, the combined pharyngeal-gastric access channel 40 can be about 5 mm in diameter to allow for the passage of a size 14 F gastric tube. The combined pharyngeal-gastric access channel 40 travels alongside the right lateral side of the airway channel 20, and continues onto the back plate 11 of the mask portion 102 until the combined pharyngeal-gastric access channel 40 reaches a lower part of the back plate 11, at which it curves toward a midline of the back plate 11 of the mask portion 102 and terminates as the ampulla 43 at the apex 17 of the mask portion 102 (FIGS. 1 and 2). The ampulla has a distal opening 42 which opens to the upper esophagus when the airway device 100 is place inside the upper airway. As a result, the ampulla 43 and combined pharyngeal-gastric access channel 40 system can vent air leak from the airway, preventing gastric insufflation, and can evacuate residual gastric fluid with a gastric tube, preventing aspiration. The ampulla 43 is also connected to the pharyngeal sump channels 50 as described herein and serves as an exit bay for pharyngeal secretions, further preventing aspiration or laryngospasm. This combination design allows for evacuation of gastric fluid from the esophagus and stomach, or air leakage from the airway, as well as secretions or bleeding from the pharynx all through one channel.

To ensure efficacy and safety, embodiments of the multi-channel airway device 100 described herein may have several features including: 1) a large airway lumen of the airway channel 20 for easy passage of an endotracheal tube or an endobronchial tube such as an embodiment of the endobronchial isolation tube (BIT) described herein; 2) the imaging channel 30 configured to house an imaging device for confirmation of adequate placement of the mask portion 102, and for visualization and monitoring of the glottis; and 3) a combined pharyngeal-gastric access channel 40 for evacuation of residual gastric content as well as pharyngeal secretions or other body fluids. In an exemplary embodiment, the airway device 100 may provide access and ventilation to both lungs during two-lung ventilation, or to the healthy non-operative lung during one-lung ventilation when the contralateral lung is blocked by the BIT. In addition, and in an exemplary embodiment, the airway device 100 may provide a conduit for the placement of the BIT or a regular tracheal tube.

In an exemplary embodiment, the airway device 100, as described herein, may provide ventilation and access to both lungs during two-lung ventilation, and to the healthy non-operative lung during one-lung ventilation when the contralateral lung is isolated and accessed by an embodiment of the BIT. The multi-channel airway device 100 may include, in addition to the large main airway channel 20, two other channels to ensure the efficacy and safety of lung separation.

First, the open-ended imaging channel 30 may travel along the airway channel 20 and then may merge into the airway channel 20 distally, and may be used to visualize both the glottis (at variable distances) and the trachea using a flexible bronchoscope, which may allow for confirmation of adequate placement of the mask portion 102, and may guide the placement of the BIT through the trachea into the bronchus. Furthermore, the imaging channel 30 may be equipped with the removable inner tube 34 which may house the imaging device and may protect it from direct contact with the patient when access of the trachea by the bronchoscope is not needed. Second, the combined pharyngeal-gastric access channel 40 may follow the airway channel 20 and the back plate 11 to the apex 17 of the mask portion 102 and may allow for evacuation of gastric residuals or air leakage as well as pharyngeal secretions or other body fluids, thereby ensuring the function of the airway device 100 and minimizing or eliminating the risk of gastric insufflation, aspiration and laryngospasm. The design of the airway device 100 may ensure the multiple functionalities of the airway device without rendering the airway device 100 unwieldy or difficult to construct.

Figure 5A:
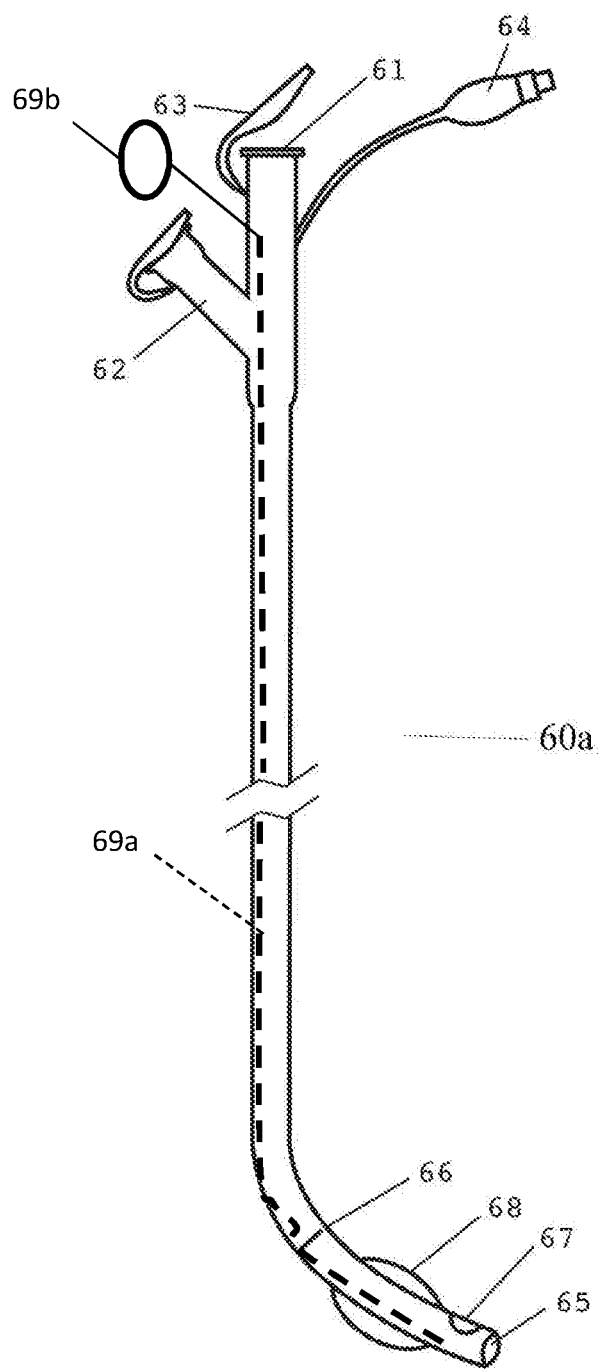
FIG. 5A illustrates a perspective view of the left bronchial isolation tube showing a main or bronchoscope port and a side or ventilation-CPAP port with caps, a curved and flexible distal portion with a 5-mm marker-line, a murphy eye, and a balloon and its inflation pilot and according to aspects described in the present disclosure.
Figure 5B:
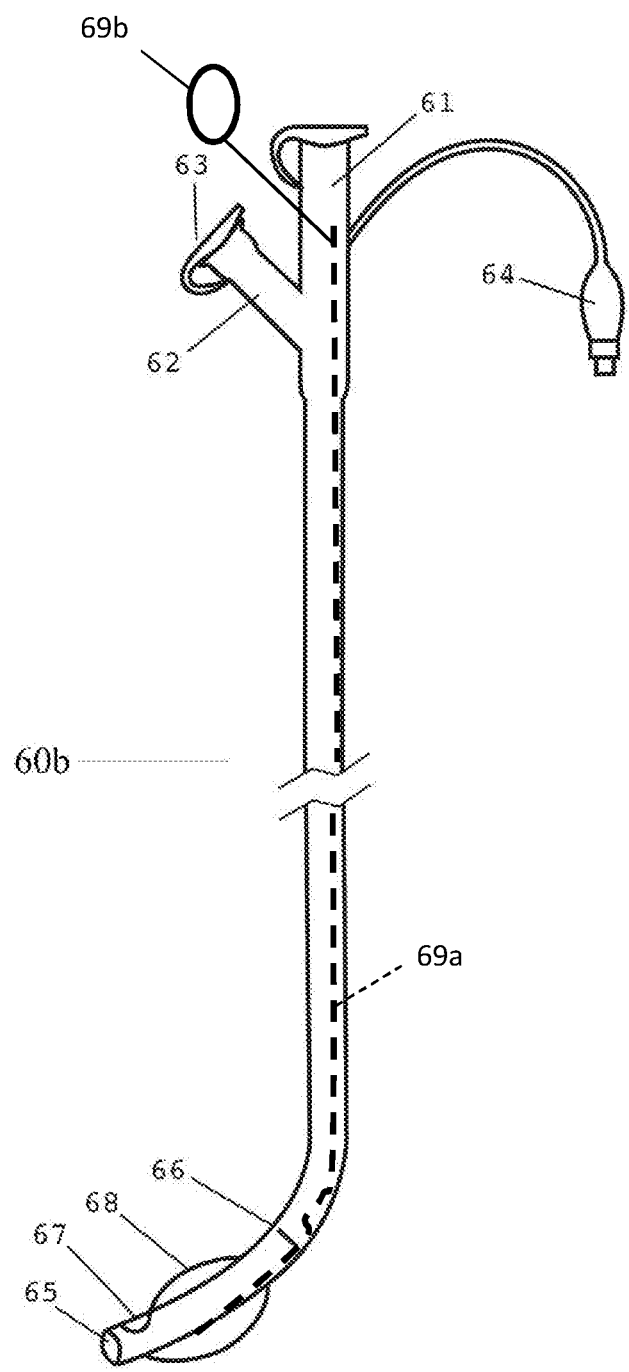
FIG. 5B illustrates a perspective view of the right bronchial isolation tube showing a main or bronchoscope port and the side or ventilation-CPAP port with caps, a curved and flexible distal portion with a 5-mm marker-line, a murphy eye, and a balloon and its inflation pilot according to aspects described in the present disclosure.

In an exemplary embodiment, as shown in FIGS. 5A and 5B, bronchial isolation tubes (BITs) 60a and 60b, respectively, may be an elongated endobronchial tube that has a proximal Y-end with a center 61 and a side port 62, and a flexible and/or curved distal end. The BIT 60a or 60b may be formed such that it is small enough to be inserted, via embodiments of the airway device 100, into the bronchus to isolate the lungs, and large enough to provide both ventilation and access to the ipsilateral lung. Functionally, the BIT 60a or 60b may serve to isolate the operative or diseased lung, and also to provide adequate access to the ipsilateral lung for aspiration, lavage, bronchoscopy, application of continuous positive airway pressure, as well as independent ventilation. With a flexible and soft distal portion, the BIT 60a or 60b may be less likely to cause injury to the airway when compared with a DLT, and may be easier to place when compared to bronchial blockers. Moreover, because the BIT 60a or 60b can be placed through the airway channel 20 of an embodiment of the airway device 100, the BIT 60a or 60b may be used in patients with difficult airway in which situation a laryngeal mask is often used to rescue and manage the patient's airway. Unlike the traditional endobronchial tube, the BIT 60a or 60b may be placed in the main bronchus of the surgical or diseased side of the lungs. The BIT 60a or 60b may be removed toward the end of surgery while using the airway device 100 to manage ventilation, thereby avoiding airway irritation during emergence from anesthesia. When postoperative ventilation is needed, the airway device 100 may be left in place for a short duration, or a regular tracheal tube may be introduced through the airway device 100.

With its supraglottic approach, a system that includes an embodiment of the airway device 100 and the BIT 60a or 60b assembly described herein may provide a less traumatic alternative for lung isolation and one-lung ventilation in general. Additionally, in patients with difficult airway who require lung separation and access to the diseased lung, this method may be more feasible and practical to use because, for these patients, a DLT is difficult or impossible to place while a bronchial blocker is of limited use. Therefore, the system including the airway device 100 and the BIT 60a or 60b, as taught herein, may be used to offer the benefits of both the DLT and the bronchial blocker, while avoiding the disadvantages of either individually.

Referring still to FIGS. 5A and 5B, a bronchial isolation tube (BIT) 60*a* and 60*b*, respectively, are described herein. The BITs 60*a* and 60*b* are each an elongated endobronchial tube with a curved and/or flexible distal portion that fits in and opens to the lumen of the main bronchus. The BIT 60*a* and 60*b* are approximately 42 cm in length so that they, when used in an average-sized adult, extend from the bronchus through the trachea and the airway channel out of the swivel adaptor. The BIT 60*a* or 60*b* can have an inner diameter of approximately 4 mm to 6 mm to allow for bronchoscopy. A distal portion includes a murphy eye 67, and has a low-pressure inflatable member or balloon 68 to block and isolate the operative lung, as well as a mark-line indicator 66 that is 5 mm proximal to the balloon 68. The balloon 68 is made of colored material for easy recognition, and is connected by an inflation line to a pilot 64 for inflation. A tip 65 of at a (bronchus) distal end of the BIT 60*a* or 60*b* can be made of soft material. The optional steering assembly can include a wire 69*a* disposed along the first and second elongated tube portions and a steering member 69*b* may be disposed at the proximal end of the bronchial isolation tube. The wire 69*a* can be embedded in the wall of the BIT 60*a* or 60*b* to adjust the angle of the flexible distal portion, with a steering mechanism 69*b* assembled at the proximal end. The steering member 69*b* may be operatively coupled to the wire 69*a* and configured to manipulate the wire 69*a* to adjust the angle at which the second elongated tube portion extends relative to the first elongated tube portion. This adjustable and flexible distal portion facilitates passage of the BIT 60*a* or 60*b* through the glottis and into the bronchus.

Figure 7A:
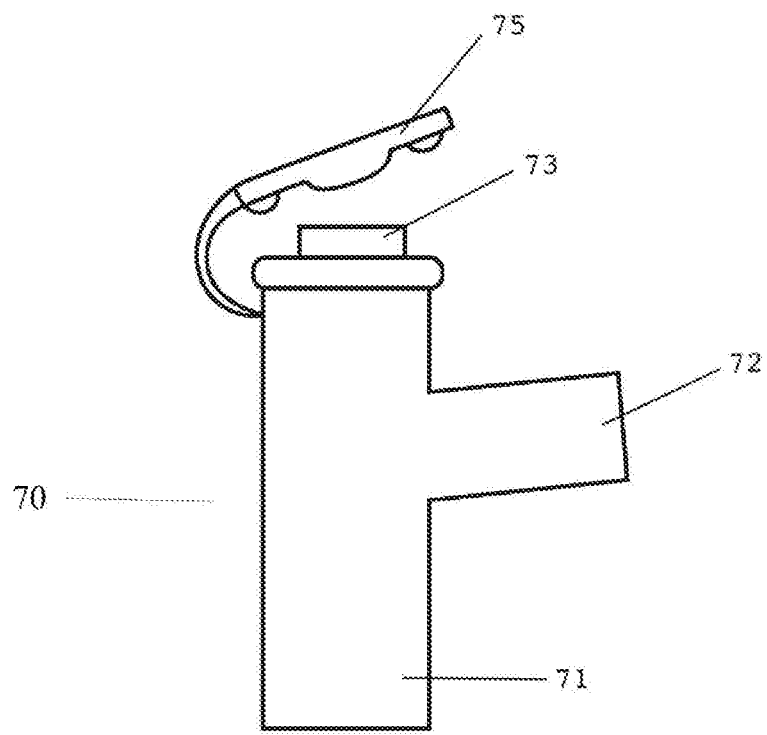
FIGS. 7A and 7B illustrate a perspective view of an exemplary swivel adaptor according to aspects of the present disclosure, wherein a laryngeal mask connector, a circuit port, a bronchial isolation tube (BIT) (center) port and a cap and the modified swivel adaptor with a bronchoscope (side) port are shown.
Figure 7B:
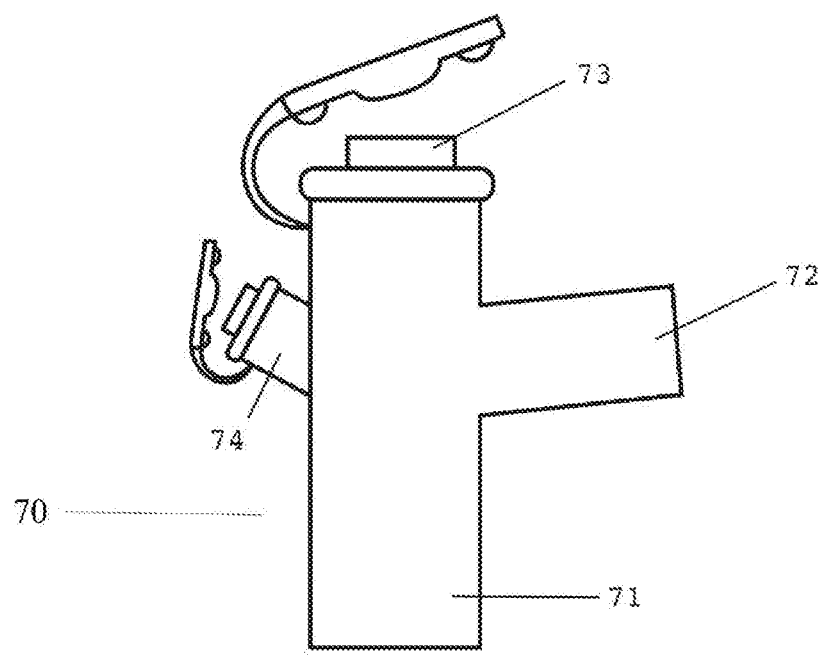
Figure 8:
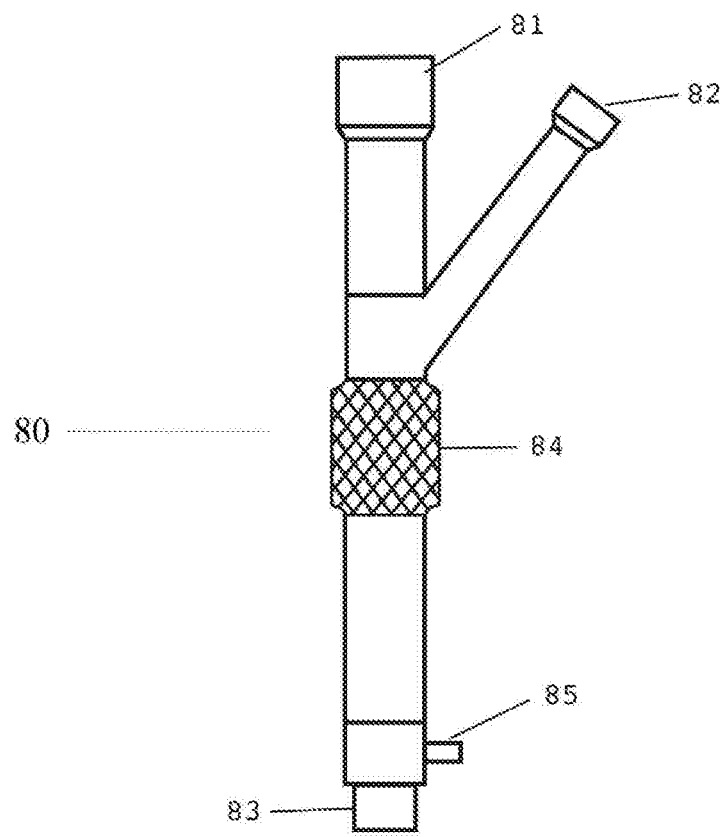
FIG. 8 illustrates a perspective view of an exemplary connector according to aspects of the present disclosure described herein, showing a corrugated 3-way connecting tube that fits a laryngeal mask on one end and a standard anesthesia circuit on the other end, and has a bronchial adaptor that fits to the side port of an embodiment of the bronchial isolation tube (BIT), a built-in thermo-moisture filter and a $CO_2$ sampling port.

Proximally, the BITs 60*a* and 60*b* each terminate as a two-port Y-structure, with a center or main port 61 for bronchoscope and aspiration, and a side port 62 for application of CPAP or for connection to the ventilator via a connector 80 (FIG. 8). The two ports are sealed and capped with a cap 63 when access is not needed. In addition, as shown in FIGS. 7A and 7B, a swivel adaptor 70 mounts the BIT to embodiments of the airway device 100, and can connect the airway device 100 to a ventilator.

The BIT 60*a* or 60*b* can be either left-sided or right-sided, depending on the length and the angle of its flexible distal portion, and therefore can block either the left or right lung. The BIT 60*a* can form a left-sided BIT, and a distal portion of a left-sided BIT can be about 40 to 50 mm in length, curved at 40~50 degrees with the balloon 68 located just proximal to a murphy eye 67. The balloon 68 of the left-sided BIT 60*a* can have a regular circle or spherical shape. The BIT 60*b* can form a right-sided BIT, and a distal portion of a right-sided BIT can be shorter than that of the left-sided BIT, about 25~35 mm, curved at about 30 degrees with a balloon that surrounds but does not cover or obstruct the murphy eye. For example, the balloon can have an irregular or asymmetrical shape.

Figure 6A:
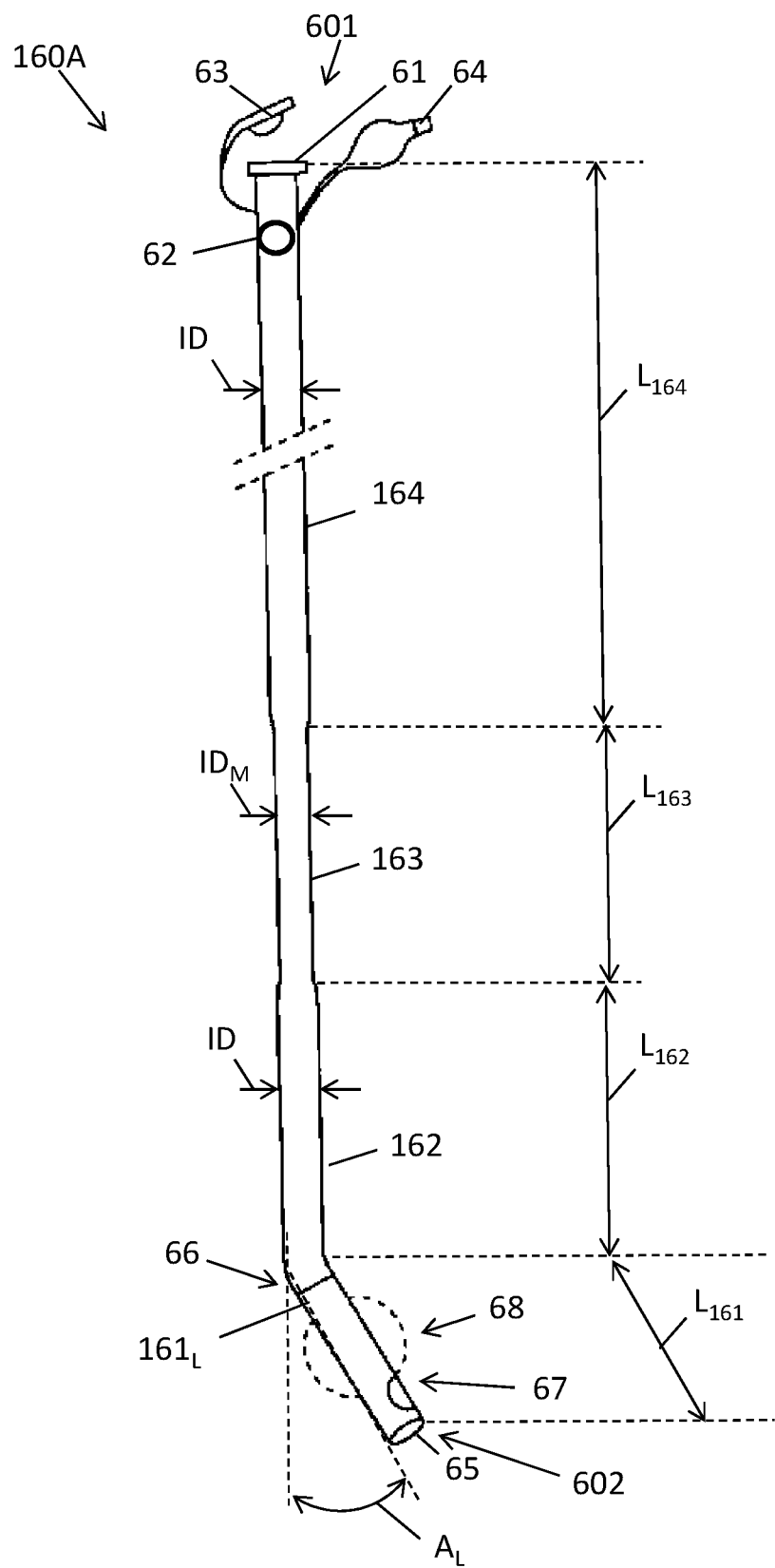
FIG. 6A illustrates a perspective view of a left bronchial isolation tube showing a center bronchoscope port with a seal and a cap, a side port for ventilation, a curved and/or flexible distal portion with a 5-mm marker-line, a murphy eye, and a cuff and its inflation pilot according to aspects described in the present disclosure.
Figure 6B:
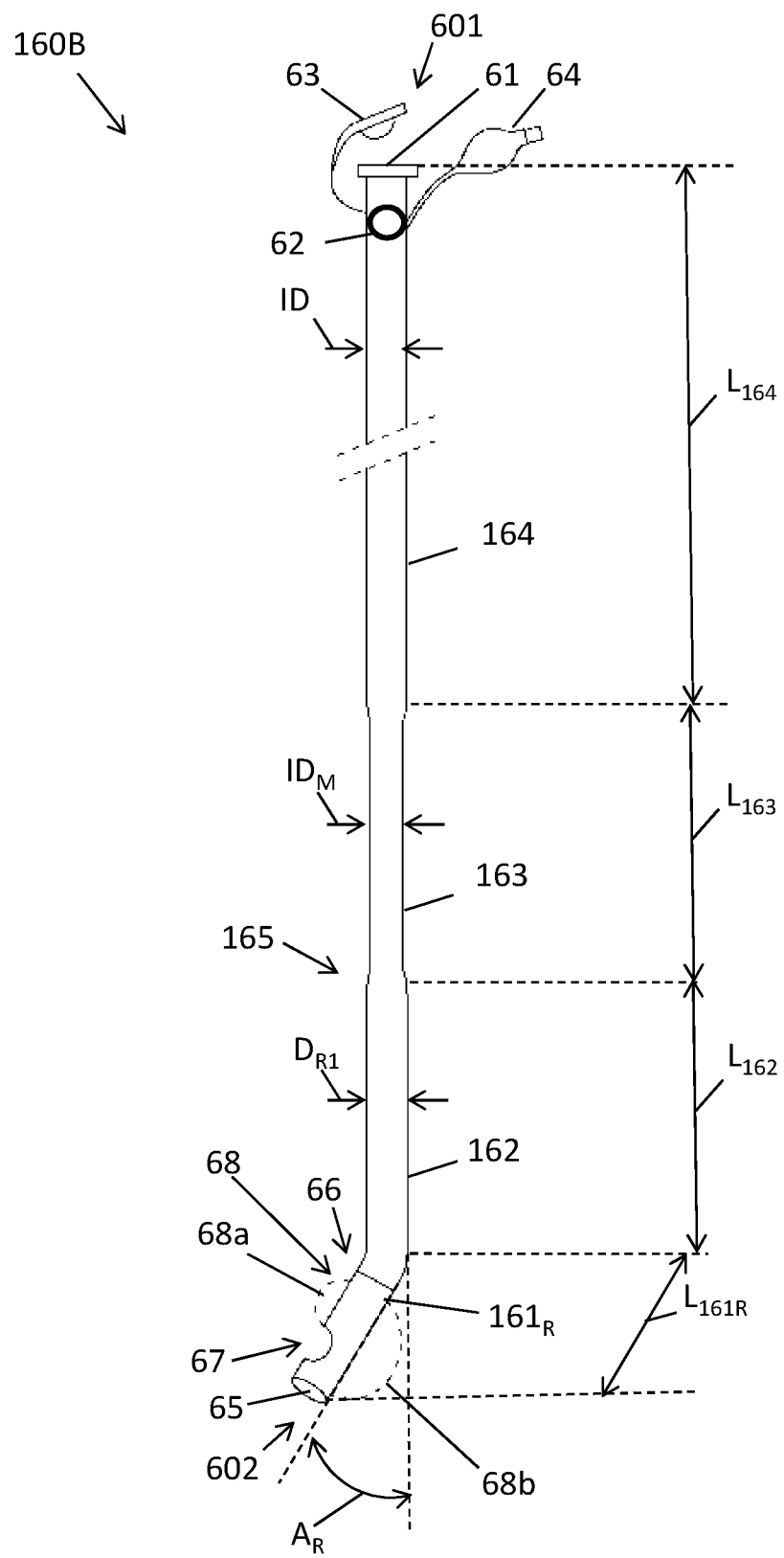
FIG. 6B illustrates a perspective view of a right bronchial isolation tube showing a center bronchoscope port with a seal and a cap, a side port for ventilation, a curved and/or flexible distal portion with a 5-mm marker-line, a murphy eye, and a cuff and its inflation pilot according to aspects described in the present disclosure.

FIGS. 6A-B illustrate exemplary embodiments of bronchial isolation tubes (BITs) 160A and 160B, respectively. The BITs 160A and 160B can be elongated endobronchial tubes that have an elongated tubular body with a flexible and/or curved distal end. A portion of the elongated tubular body can have a reduced outer and inner diameters as compared to a remainder of the elongated tubular body such that the portion of the elongated tubular body having the reduced outer and inner diameters is positioned across a glottis of a human when the distal end of the elongated tubular body is positioned in the bronchus of the human. The BITs 160A and 160B can each be stand-alone devices for insertion into an airway and a bronchus of a patient and/or can be used with an airway device or laryngeal mask, such as for example, an embodiment of the airway device 100 or other airway devices. The BITs 160A and 160B can have a length that is measured along a central axis of the BITs 160A and 160B from a proximal end 601 to a distal end 602 of the BITs 160A and 160B. In an exemplary embodiment, the BIT 160B can have a length of approximately 330 mm to approximately 450 mm and the BIT 160A can have a length of approximately 345 mm to approximately 465 mm so that they can extend from a swivel adaptor through the airway channel and the trachea to the target bronchus in a patient. For example, in a non-limiting example embodiment, one size of the BIT 160B can have a length of approximately 410 mm and one size of the BIT 160A can have length of approximately 425 mm so that they can extend from a swivel adaptor through the airway channel and the trachea to the target bronchus in an average-sized adult.

The BITs 160A and 160B can be formed of PVC or similar materials with suitable firmness for insertion into and through an airway device. As a non-limiting example, the elongated tubular body of the BITs 160A and 160B can have a thickness of approximately 0.5 mm to approximately 1.0 mm or approximately 0.8 mm. In exemplary embodiments, the elongated tubular bodies of the BITs 160A and 160B can have a uniform thickness along their lengths such that the difference between the inner diameter and the outer diameter of the BITs 160A and 160B can correspond to the thickness. For example, if the inner diameter of a portion of the BIT 160A or 160B is 4.5 mm, the outer diameter of the portion of the BIT 160A or 160B is 4.5 mm plus the thickness of the elongated tubular body (e.g., if the inner diameter is 4.5 mm and the thickness is 1 mm, then the outer diameter is 5.5 mm).

The proximal center port 61 can be used for bronchoscopy or CPAP and can be sealed and capped with a cap 63 when access is not needed. Additionally, the upper portion includes a side port 62 which can be connected via a connector to the circuit of a ventilator or an anesthesia machine. A flexible and soft distal portion of the BITs 160A and 160B may be less likely to cause injury to the airway of a patient when compared with a DLT, and may be easier to place when compared with bronchial blockers.

The BITs 160A and 160B may be formed such that they have an outer diameter that is small enough to be inserted, via embodiments of the airway device 100 or other airway devices, into a bronchus to isolate the lungs, and yet have an inner diameter that is large enough to provide both ventilation and access to the ipsilateral lung. Functionally, the BITs 160A or 160B may serve to isolate the operative or diseased lung, and also to provide adequate access to the ipsilateral lung for aspiration, lavage, bronchoscopy, application of continuous positive airway pressure (CPAP), as well as independent ventilation. Moreover, because the BITs 160A or 160B can be placed through an airway channel of an airway device (e.g., such as the airway channel 20 of the airway device 100), the BITs 160A or 160B may be used in patients with difficult airways in which situations a laryngeal mask is often used to rescue and manage the patient's airway. Like a traditional endobronchial tube, the BIT 160A or 160B can be placed in a bronchus to provide ventilation to the ipsilateral lung. Unlike the traditional endobronchial tube, the BITs 160A or 160B may also be placed in the main bronchus of the surgical or diseased side of the lungs to provide isolation and/or deflation (collapse) as well as access for bronchoscopy, lavage, CPAP or ventilation whenever needed. The BITs 160A or 160B may be removed toward the end of surgery while using the airway device 100 to manage ventilation, thereby avoiding airway irritation during emergence from anesthesia. When postoperative ventilation is needed, the airway device 100 may be left in place for a short duration, or a regular tracheal tube may be introduced through the airway device 100.

As shown in FIGS. 6A-B, the BITs 160A and 160B can include four sections: a distal section 161, a lower section 162, a middle section 163, and an upper section 164. The middle section 163 is disposed between, and has a smaller in inner and outer diameter than the distal, lower, and upper sections 161, 162, and 164. The BIT 160A and 160B can have a uniform inner diameter ID along its length except in the middle section 163 where the elongated tubular body has an inner diameter $ID_M$ that is approximately 0.5 mm to approximately 1.5 mm smaller than the inner diameter ID of remainder of the elongated tubular body (i.e. the distal, lower, and upper sections). The outer diameter of the middle section 163 is also approximately 0.5 mm to approximately 1.5 mm smaller than the outer diameter of the remainder of the elongated tubular body (i.e. the distal, lower, and upper sections). For example, the inner diameter $ID_M$ can be approximately 0.5 mm to approximately or approximately 1.5 mm or approximately 10 percent to approximately 20 percent smaller than the inner diameter ID. Likewise, because the outer diameter corresponds to the inner diameter, the outer diameter of the middle section 163 can be smaller than the outer diameter of the rest of the elongated tubular body by approximately 0.5 mm to approximately 1.5 mm or approximately 10 percent to approximately 20 percent. The BITs 160A and 160B advantageously provide improved aerodynamics by offering a larger diameter without blocking airflow through the glottis because of the narrower outer and inner diameter of the middle portion defined by the middle section 163. In exemplary embodiments, the BITs 160A and 160B can have an inner diameters ID of approximately 4.5 mm to approximately 6.0 mm with the inner diameter of the middle section $ID_M$ of approximately 4.0 mm to approximately 5.0 mm, respectively, where the difference between the inner diameter ID and the inner diameter $ID_M$ is approximately 0.5 mm to approximately 1.5 mm.

The length of the BIT is designed to extend from above the swivel adaptor and the airway channel of a laryngeal mask or other airway device through the glottis and the trachea to the entrance of a bronchus. A length $L_{164}$ of the upper section 164 can be approximately 210 mm to approximately 250 mm or about 230 mm so that this section can extend from above the glottis through the human upper airway or the airway channel of a laryngeal mask or another airway device, and can extend to outside the airway. As a non-limiting example, the BIT 160A and 160B can be made in three different overall lengths (S, M and L), where the upper section 164 can have lengths of approximately 210 mm, 230 mm and 250 mm, respectively, to be used for people of different height or anatomical respiratory characteristics.

The length $L_{163}$ of the middle section 163 can be approximately 40 mm to approximately 60 mm or approximately 50 mm so that when the BIT is placed as instructed, the narrower middle section 163 extends across the human glottis. The length $L_{163}$ can be relatively fixed and can be independent relative to the lengths of the upper, lower, and distal sections or the overall length of the elongated tube.

The length $L_{162}$ of the lower section 162 can be approximately 80 mm to approximately 120 mm or approximately 100 mm, so that this section can extend nearly the length of the human trachea, which can be approximately 100 mm to approximately 140 mm in length. As a non-limiting example, the BIT 160A and 160B can be made in the three different lengths/sizes (S, M and L), where the lower section has lengths of 80 mm, 100 mm and 120 mm, respectively, to be used for people of different height or with different anatomical respiratory characteristics.

The distal section 161 defines the differences between the left and right BIT 160A and 160B. The length $L_{161L}$ of the distal section $161_L$ of the left BIT 160A can be approximately 45 mm. The length $L_{161R}$ of the distal section $161_R$ of the right BIT 160B can be approximately 30 mm. For the left BIT 160A, the distal section $161_L$ can extend at an angle $A_L$ relative to the upper, middle, and lower sections; and for the right BIT 160B, the distal section $161_R$ can extend at an angle $A_R$ relative to upper, middle, and lower sections. In exemplary embodiments, the angles $A_R$ and $A_L$ can be approximately 0 degrees to approximately 50 degrees relative the upper, middle, and lower sections. For example, in an exemplary embodiment, the angle $A_R$ can be approximately 25 to 35 degrees or approximately 30 degrees to bias the right bronchus, and the angle $A_L$ can be approximately 40 to 50 degrees or approximately 45 degrees to bias the left bronchus. If the distal section 161 is soft enough, angle $A_L$ or $A_R$ can be zero or nearly zero.

At the distal end 602, the distal port 65 opens to the lumen of a bronchus when the BBT 160A or 160B is positioned in the airway and bronchus of a human. Additionally, the distal section $161_L$ and $161_R$ can include the Murphy eye 67, which can be formed proximally to the distal end 602 and immediately adjacent to the distal port 65; the low-pressure inflatable member 68 (e.g., a cuff or balloon) that is approximately 20 mm in length and can be inflated with air to block and isolate the ipsilateral lung; and a mark-line indicator 66 that is proximal to and spaced approximately 5 mm apart from the inflatable member 68. The inflatable member 68 can be made of colored material for easy recognition and can be connected to a pilot balloon 64 located at the top of the tube by an inflation line embedded in the wall of the BIT.

The inflatable member 68 of the left BIT 160A can be symmetrically formed about the distal section $161_L$ of the elongated tubular body between the Murphy eye 67 and the mark-line indicator 66 such that the inflatable member 68 forms a generally spherical or cylinder shape approximately 20 mm in length. The inflatable member 68 of the right BIT 160B can be asymmetrically formed about the distal section $161_R$ of the elongated tubular body between the distal end 602 and the mark-line indicator such that the inflatable member 68 includes a short axis 68a that is approximately 10 mm in length and extends between the Murphy eye 67 and the mark-line indicator 66 so that this half of the inflatable member 68 does not interfere with or cover the Murphy eye 67, and includes a long axis 68b that is approximately 20 mm in length and generally extends about the tube opposite to the Murphy eye 67 between the distal end 602 and the mark-line. When inflated with air, the inflatable member 68 can be wide enough to block and seal the bronchus with appropriate pressure to isolate the lung corresponding to the bronchus within which the BBT 160A or 160B is placed.

In exemplary embodiments, as shown in Tables 1 and 2, the BITs can be made of two type, the left BIT 160A and the right BIT 160B (depending on the length, inflatable member and angle of the distal section), in three different exemplary non-limiting sizes (#4.5, #5.0 and #5.5 with inner diameters ID of 4.5 mm, 5.0 mm and 5.5 mm, respectively) and in three different exemplary non-limiting lengths (S, M and L with overall length of 370 mm, 410 mm and 450 mm, respectively, for the right BIT 160B and with overall length of 385 mm, 425 mm and 465 mm, respectively, for the left BIT 160A).

The middle section can correspond to ten percent to twenty percent of the length of the elongated tubular body; can begin approximately two-hundred ten millimeters to approximately two-hundred fifty millimeters from the proximal end of the elongated tubular body; and/or can end approximately two-hundred sixty millimeters to approximately three hundred millimeter from the proximal end of the elongated tubular body. The upper section can be four to six times longer than the middle section and/or the lower section can be approximately two to three times longer than the middle section. The middle section can have a length of approximately 40 millimeters to approximately 60 millimeters or can have a length of approximately 50 mm. The inner diameter of the middle section $ID_M$ can be 4.0 mm to 5.0 mm.

With reference to Table 1, exemplary non-limiting lengths of a #5 S left BIT can measure 210 mm in the upper section 164, 50 mm in the middle section 163, 80 mm in the lower section 162 and 45 mm in the distal section 161$_L$, with an inner diameter ID 5.0 mm, an inner diameter $ID_M$ of 4.0 mm to 4.5 mm, and overall length 385 mm; a #5 M left BIT can measure 230 mm in the upper section 164, 50 mm in the middle section 163, 100 mm in the lower section 162 and 45 mm in the distal section 161$_L$, with an inner diameter ID 5.0 mm, an inner diameter $ID_M$ of 4.0 mm to 4.5 mm, and overall length 425 mm; a #5 L left BIT measures 250 mm in the upper section 164, 50 mm in the middle section 163, 120 mm in the lower section 162 and 45 mm in the distal section 161$_L$, with an inner diameter ID 5.0 mm, an inner diameter $ID_M$ of 4.0 mm to 4.5 mm, and overall length 465 mm. The lengths of the short, medium, and long left BITs can be identical to #5 (ID=5 mm) for #5.5 (ID=5.5. mm) and #4.5 (ID=4.5 mm) sized inner diameters.

TABLE 1

Non-limiting exemplary lengths in millimeter (mm) for short, medium, and long left BITs described herein

|  | Short (S) | Medium (M) | Long (L) |
|---|---|---|---|
| Upper Section | 210 | 230 | 250 |
| Middle Section | 50 | 50 | 50 |
| Lower Section | 80 | 100 | 120 |
| Distal Section | 45 | 45 | 45 |
| Overall Length | 385 | 425 | 465 |

With reference to Table 2, exemplary non-limiting lengths of a #5 S right BIT can measure approximately 210 mm in the upper section 164, approximately 50 mm in the middle section 163, 80 mm in the lower section 162, and 30 mm in the distal section 161$_R$, with an inner diameter ID 5.0 mm, an inner diameter $ID_M$ of 4.0 mm to 4.5 mm, and overall length 370 mm; a #5 M right BIT can measure 230 mm in the upper section 164, 50 mm in the middle section L163, 100 mm in the lower section 162 and 30 mm in the distal section 161$_R$, with an inner diameter ID 5.0 mm, an inner diameter $ID_M$ of 4.0 mm to 4.5 mm, and overall length 410 mm; a #5 L right BIT can measure 250 mm in the upper section 164, 50 mm in the middle section 163, 120 mm in the lower section L162 and 30 mm in the distal section 161$_R$, with an inner diameter ID 5.0 mm, an inner diameter $ID_M$ of 4.0 mm to 4.5 mm, and overall length 450 mm. The lengths of the short, medium, and long left BITs can be identical to #5 (ID=5 mm) for #5.5 (ID=5.5. mm) and #4.5 (ID=4.5 mm) sized inner diameters.

TABLE 2

Non-limiting exemplary lengths in millimeter (mm) for short, medium, and long right BITs described herein

|  | Short (S) | Medium (M) | Long (L) |
|---|---|---|---|
| Upper Section | 210 | 230 | 250 |
| Middle Section | 50 | 50 | 50 |
| Lower Section | 80 | 100 | 120 |
| Distal Section | 30 | 30 | 30 |
| Overall Length | 370 | 410 | 450 |

In exemplary embodiments, as shown in Tables 3, the left BIT 160A and the right BIT 160B can be made in three different exemplary non-limiting sizes (#4.5, #5.0 and #5.5 with inner diameters ID of 4.5 mm, 5.0 mm and 5.5 mm, respectively, and $ID_M$ of 0.5 to 1.5 mm smaller than the inner diameter ID) and in two different exemplary non-limiting lengths, regular or normal (N) and extra-long (XL) with overall length of 420 mm and 460 mm, respectively, for the right BIT 160B and with overall length of 435 mm and 475 mm, respectively, for the left BIT 160A).

TABLE 3

Non-limiting exemplary lengths in millimeter (mm) for regular (N) and long (XL) BITs described herein

|  | Left BIT | | Right BIT | |
|---|---|---|---|---|
|  | Regular (N) | Long (XL) | Regular (N) | Long (XL) |
| Upper Section | 250 | 250 | 250 | 250 |
| Middle Section | 60 | 60 | 60 | 60 |
| Lower Section | 80 | 120 | 80 | 120 |
| Distal Section | 45 | 45 | 30 | 30 |
| Overall Length | 435 | 475 | 420 | 460 |
| ID | 4.5, 5.0, 5.5 | | 4.5, 5.0, 5.5 | |

Similarly, an extra-small BIT (XS) can be made for use in smaller adult patients, for example, with an inner diameter ID of 4.0 mm and overall length of 385 mm for a left #4.0 BIT and 375 mm for a right #4.0 BIT, respectively. The BIT can also be made for use in pediatric patients. As the narrowest part of the airway in children younger than ten-year-old is the subglottic area at the level of the cricoid cartilage, it is probably easier to make the pediatric BIT with an even diameter consisting of the distal section and the main body.

FIGS. 7A and 7B illustrate a perspective view of an exemplary swivel adaptor 70 according to aspects of the present disclosure. The swivel adaptor 70 can include an airway device connector 71 that engages the airway device 100, a circuit port 72 to connect the ventilator, a BIT (center) port 73 for insertion of a BIT and a cap 75, and a modified swivel adaptor with a bronchoscope (side) port 74. As one example, a dual clamp system defined as a large clamp to hold under the top edge of an adapter or the airway device 100 and a smaller clamp to hold the bronchial isolation tube or a tracheal tube may join the multiport adaptor or the laryngeal mask and the bronchial isolation tube or a tracheal tube together when the bronchial isolation tube or a tracheal tube is inserted through the adapter and/or the airway device 100 into a patient airway.

FIG. 8 depicts a perspective view of the connector 80. The connector 80 is a corrugated 3-way connecting tube that is configured to fit and mount on the airway device 100 or other airway devices at one end (airway end) 81 of the connector 80, and has a bronchial adaptor 82 that fits to the BIT. The other end (ventilator end) 83 is configured to connect to a standard anesthesia circuit. The connector 80 also includes a built-in thermo-moisture filter 84 and a $CO_2$ sampling port 85.

Figure 9:
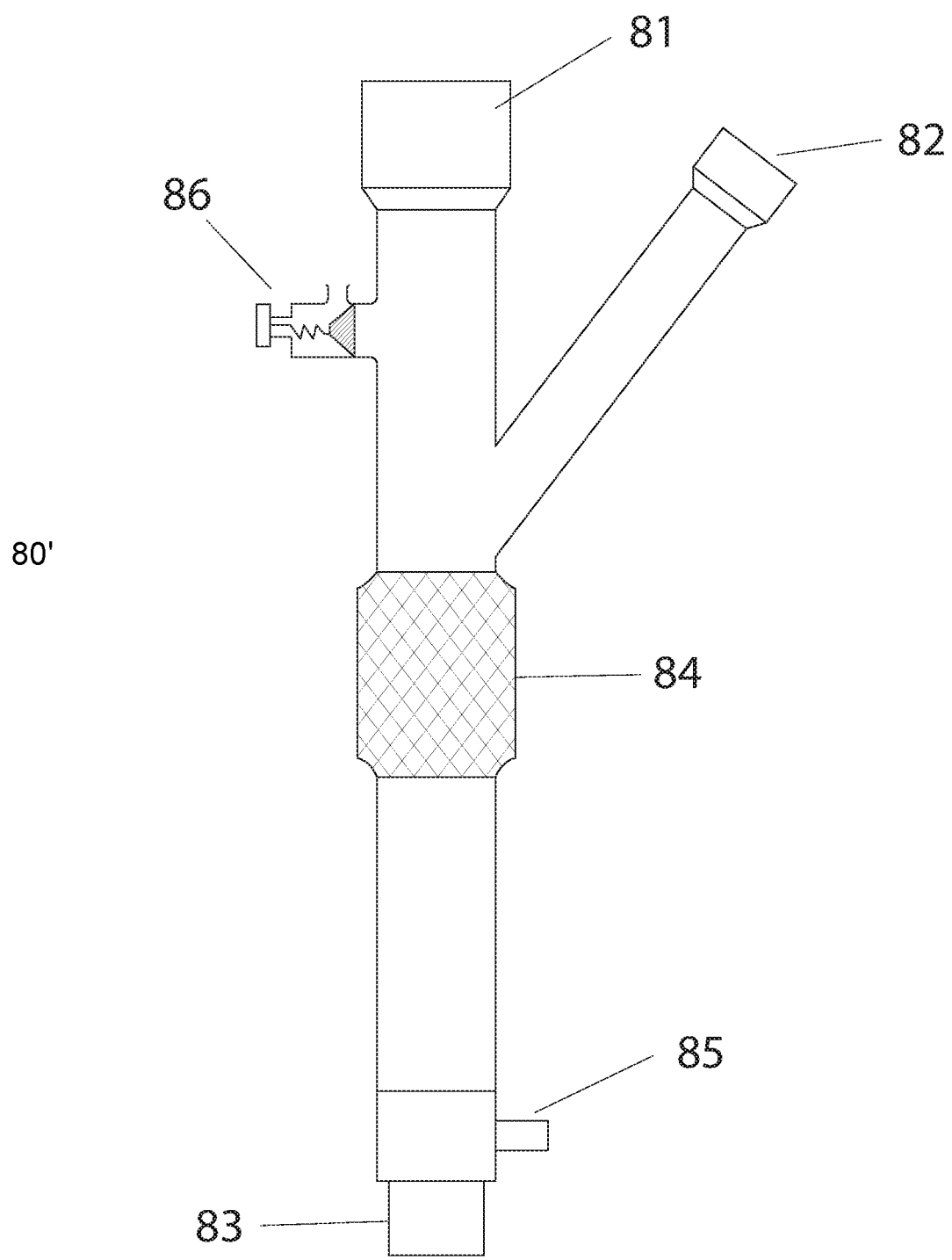
FIG. 9 illustrates a perspective view of an exemplary connector according to aspects of the present disclosure described herein, showing a corrugated 3-way connecting tube that fits a laryngeal mask on one end, which has a pressure relief valve, and a standard anesthesia circuit on the other end, and has a bronchial adaptor that fits to the bronchial isolation tube (BIT), a built-in thermo-moisture filter and a $CO_2$ sampling port.

FIG. 9 depicts a perspective view of the connector 80'. The connector 80' is a corrugated 3-way connecting tube that is substantial similar to the connector 80 except for the differences described herein. The connector 80' includes components 81-85 described with reference to FIG. 8 and also includes a pressure relief valve 86 disposed proximate to the airway end 81 of the adapter 80'. In exemplary embodiments, the connector 80' can be configured to fit and mount on the airway device 100 or other airway devices. The pressure relief valve 86 can be positioned along a shaft of the connector 80' so that it is positioned close to the airway end 81 but away from the bronchial adapter 82. The pressure relief valve 86 can be a one-way or check valve that permits air to pass through the valve in one direction. In the present embodiment, the check valve can be configured to allow air to escape from the shaft of the connector to the atmosphere. The pressure relief valve 86 can limit pressure through the airway device (e.g., a laryngeal mask) but ensure higher pressure to the BIT.

The system including the airway device 100 and the BITs 60*a*, 60*b*, 160A, and/or 160B as described herein, may be used in the following manner with reference to FIG. 10. First, after induction of general anesthesia, with or without, muscle relaxation as clinically indicated, the multi-channel airway device 100 is placed in the patient's airway, with the patient in either the supine or lateral position. The airway device 100 can be positioned in a hypopharyngeal area of a patient to cover and seal around a glottis of the patient. The airway device 100 is then connected to the anesthesia circuit through the swivel adaptor 70. Before or immediately after initiation of positive ventilation, a gastric suction tube or similar catheter is inserted through the combined pharyngeal-gastric access channel 40 into the stomach of the patient to remove any residual gastric fluids. Generally, easy passage of the gastric suction tube indicates adequate placement of the airway device 100. After confirmation of effective ventilation via the airway device 100 using the conventional method, adequate depth of anesthesia and muscle relaxation should be ensured from this point forward to prevent coughing or laryngospasm during subsequent steps.

A flexible bronchoscope or similar imaging device can be placed through the seal ring on the first opening 31 into the imaging channel 30 to visualize the glottis and to further confirm adequate placement of the mask portion 102 of the airway device 100. After imaging confirmation, the imaging device can be pulled back slightly from the airway channel 20 and secured inside the imaging channel 30. While the patient is ventilated via the swivel adaptor through the airway device 100 with 100% oxygen, a BIT (e.g., the BIT 60*a*, 60*b*, 160A, or 160B) for the target side is inserted into the center port 73 of the swivel adaptor 70, through airway channel 20 and the glottic opening into the trachea under the guidance of the imaging device that is secured in the imaging channel 30. Once the BIT 60*a*, 60*b*, 160A, or 160B passes the vocal cords, the imaging device (e.g., a bronchoscope) is advanced into the trachea, via the merger between the imaging channel 30 and airway channel 20, to guide the further advancement of the BIT 60*a*, 60*b*, 160A, or 160B into the target bronchus (side-by-side approach). Alternatively, the BIT 60*a*, 60*b*, 160A, or 160B can be mounted on the flexible bronchoscope and inserted together via the center port 73 of the swivel adaptor 70 into the trachea (inside approach). With the aid of the imaging device or the flexible bronchoscope, either side-by-side or inside its lumen, the BIT 60*a*, 60*b*, 160A, or 160B is then further advanced and the flexible distal portion is steered, using either its steering apparatus or the bronchoscope, into the target bronchus until the balloon is about 5 mm beyond the tracheal carina (i.e. the 5 mm-mark on the BIT sits at the entry of the bronchus). Once the inflatable member 68 is inflated and the flexible bronchoscope is withdrawn, the BIT 60*a*, 60*b*, 160A, or 160B can be secured with a clip or a dual clamp or other mechanism. Both lungs are then ventilated either through the laryngeal mask airway device 100 if the BIT inflatable member is not inflated or through the laryngeal mask 100 and the BIT 60*a*, 60*b*, 160A, or 160B if the BIT inflatable member is inflated, using the connector 80 or 80' to connect the breathing circuit to the airway device 100 and the BIT 60*a*, 60*b*, 160A, or 160B.

Confirmation of effective lung isolation should be carried out using both auscultation and bronchoscopy. After the BIT 60*a*, 60*b*, 160A, or 160B is inserted in the intended main bronchus, bronchoscopy should be performed to ensure the inflated balloon is safely secured and does not block any lobar bronchi or the contralateral main bronchus. If the bronchoscope is placed side-by-side with the BIT during its insertion, the colored balloon should be seen about 5 mm inside the bronchus in order to ensure a margin of safety. The bronchoscope is then inserted into the BIT 60*a*, 60*b*, 160A, or 160B to ensure its patency and that no lobar bronchus is blocked by the tube or its balloon. This is particularly important when a right-sided BIT 60*b* or 160B is placed; its murphy eye should open to the right upper lobar bronchus. If the bronchoscope is loaded inside the BIT 60*a*, 60*b*, 160A, or 160B during its insertion (inside approach), then upon confirming the tube's patency, it should be carefully withdrawn from the BIT 60*a*, 60*b*, 160A, or 160B and placed in the trachea via the imaging channel 30 to verify the location of the colored balloon as mentioned above. Ventilation can and should continue via the airway device 100 throughout bronchoscopy.

After bronchoscopy, ventilation is then assessed through auscultation of the lungs. With the BIT 60*a*, 60*b*, 160A, or 160B secured as described above and its balloon 68 deflated, ventilation through the airway device 100 should generate breath sounds in both lungs, though the operative side may be less audible given the BIT 60*a*, 60*b*, 160A, or 160B inside the main bronchus. Then, with the balloon 68 inflated (i.e. isolation initiated), ventilation via the airway device 100 should generate breath sounds only on the side of the non-operative lung, while ventilation via the BIT 60*a*, 60*b*, 160A, or 160B should generate breath sounds only on the side of the operative lung. After confirmation of breath sounds, lung isolation and one-lung ventilation can be initiated whenever indicated by inflating the bronchial balloon 68 and ventilating through the airway device 100.

During one lung ventilation, hypoxemia and hypoxia may occur and require CPAP to provide oxygen to the operative lung to decrease shunting and improve oxygenation. This can be easily achieved by applying CPAP through the BIT 60*a*, 60*b*, 160A, or 160B. When needed, shifting to bilateral ventilation during the surgery can be immediately achieved either by deflating the bronchial balloon 68 or by ventilating the BIT 60*a*, 60*b*, 160A, or 160B and the airway device 100 simultaneously, using the connector 80 that connects both the airway device 100 and the BIT 60*a*, 60*b*, 160A, or 160B to the anesthesia circuit. If high airway pressure is needed to ventilate through the BIT, the pressure relief valve can ensure a relative lower pressure through the laryngeal mask 100. If deflation of an individual lung lobe is needed, a conventional bronchial blocker can be placed either through the BIT 60a, 60b, 160A, or 160B or, in lieu of the BIT 60a, 60b, 160A, or 160B, through the airway channel 20 of the airway device 100. On the other hand, if intubation of the trachea is necessary during the surgery, the BIT 60a, 60b, 160A, or 160B can be removed from the airway device 100, and a regular tracheal tube can be inserted through the airway channel 20 and past the glottic opening under imaging guidance, e.g., via an imaging device inserted into the imagining channel 30.

Care should be taken as follows when using the systems and apparatuses described herein. Effective ventilation is essential and should be assessed with adequate airway pressure, tidal volume, capnography waveforms and visualization. The embodiments of the airway device 100 described herein bears improved imaging channel 30 and pharyngeal-gastric channel 40 to ensure its efficacy and safety. Air leak should be checked carefully, and the cuff (inflatable member) inflation pressure of the mask portion 102 should be maintained as low as possible when an inflatable cuff is employed. A pressure gauge installed in the inflation line can help with this purpose, unless the embodiment of airway device 100 is equipped with an automatic self-inflating cuff or a non-inflatable mask. If high inflation pressure is needed to seal the air leak, a differently sized airway device 100 should be considered. Visualization of the glottis through the imaging channel 30 can help elucidate any causes of malfunction and guide clinical decision-making, which can lead to improving the seal, diagnosing obstruction or laryngospasm and avoiding gastric insufflation. As with any supraglottic airway device, air leakage and gastric regurgitation should be monitored continuously and corrected promptly throughout the operation, and oral secretions should be evacuated periodically via the pharyngeal-gastric access channel 40, particularly if the patient has large amount of secretions or other body fluids such as blood, or if the duration of the procedure is relatively long. The advantage of the pharyngeal sump channels 50 is that small amount of secretions or body fluids will be drained into the esophagus and stomach through the ampulla 43, circumventing the need of frequent suction, whereas large amount of body fluids such as active oral or nasal bleeding can be promptly removed with intermittent suction through the pharyngeal-gastric access channel 40. In addition, adequate depth of anesthesia and muscle relaxation, particularly relaxation of the central airway muscles and the vocal cords, should be maintained in order to ensure adequate glottic opening and better seal of the airway device 100, as long as the BIT 60a, 60b, 160A, or 160B is in place. The multi-channel airway device 100 offers the option of continuous monitoring of the glottis through the imaging channel 30, which helps ensure the efficacy of the airway device 100 as well.

Another unique advantage of the systems, methods and apparatuses taught herein is that induction of general anesthesia and placement of embodiments of the airway device 100 can be carried out with the patient in the lateral decubitus position, which is necessary for thoracic surgeries under most clinical situations. This way of practice ensures that the patient is comfortable in the lateral position while still awake, and therefore likely avoids position-related injury to the patient. More importantly, embodiments of the present disclosure can eliminate the potential for positional change-related malfunction and complications not uncommon to both DLT and bronchial blockers. In addition, the pharyngeal sump channels 50 and imaging channel 30 described herein may expand the clinical application of laryngeal mask airway devices and other supraglottic airway devices, while improving efficacy as well as safety.

Embodiments of the multi-channel all-purpose airway device 100 can be used alone as a regular supraglottic airway for non-thoracic surgeries, with added safety features and ease as outlined above. Briefly, after induction of general anesthesia, the multi-channel airway device 100 is placed in the upper airway of a patient, with the patient in either the supine or lateral position. The airway device 100 is then connected to the anesthesia circuit. Before or immediately after initiation of positive ventilation, a gastric suction tube or similar catheter is inserted through the pharyngeal-gastric access channel 40 into the stomach to remove any residual gastric contents. Again, easy passage of the gastric suction tube generally indicates an adequate placement of the airway device 100. The adequacy of the device positioning can be assessed generally with the conventional method. If there is any doubt or suspected malfunction or malposition of the airway device 100, a flexible bronchoscope or similar imaging device can be placed in the imaging inner tube 34, which is then inserted into the imaging channel 30. By following the colored line on the wall of the imaging channel 30 to its distal end, and further into the airway lumen of the airway channel 20, into which the imaging channel 30 merges, if necessary. The imaging device can provide visualization of the glottis, which can guide the decision-making and avoid unnecessary removal or replacement of the airway device 100. During the course of the operation, the imaging device can be left in place to monitor the dynamic of the vocal cords and to ensure the function of the airway device 100. At the end of the surgery, the stomach can be further suctioned to remove gastric residuals. The gastric tube is then gently pulled back without applying suction. When the tip of the gastric tube reaches the ampulla 43, suction is applied to remove secretions in the pharynx. These steps further decrease the risk of aspiration and laryngospasm during emergence from anesthesia while also avoiding insertion of a pharyngeal suction catheter, which is often ineffective, difficult or even infeasible.

In addition to using the BITs described herein (e.g., 60a, 60b, 160A, and 160B) with embodiments of the airway device 100 described herein, the BITs can be used in conjunction with other airway devices that have an adequately sized airway lumen, using a modified swivel adaptor (FIG. 7B), to achieve lung isolation and one-lung ventilation. After placement of the airway device, a flexible bronchoscope is inserted via the side-port 74 of the modified swivel adaptor into the airway lumen while the patient is ventilated through the circuit port 71. The BIT 60a, 60b, 160A, or 160B is then inserted via the center port 73 into the airway lumen, and under the guidance of the bronchoscope, into the trachea just below the vocal cords. The bronchoscope is then advanced into the trachea to further guide the placement of the BIT 60a, 60b, 160A, or 160B into the target bronchus as described above. However, after confirmation of the BIT placement, the bronchoscope must be removed from the airway lumen, and continuous monitoring of the glottis during the operation will no longer be accessible under this circumstance.

Figure 11:
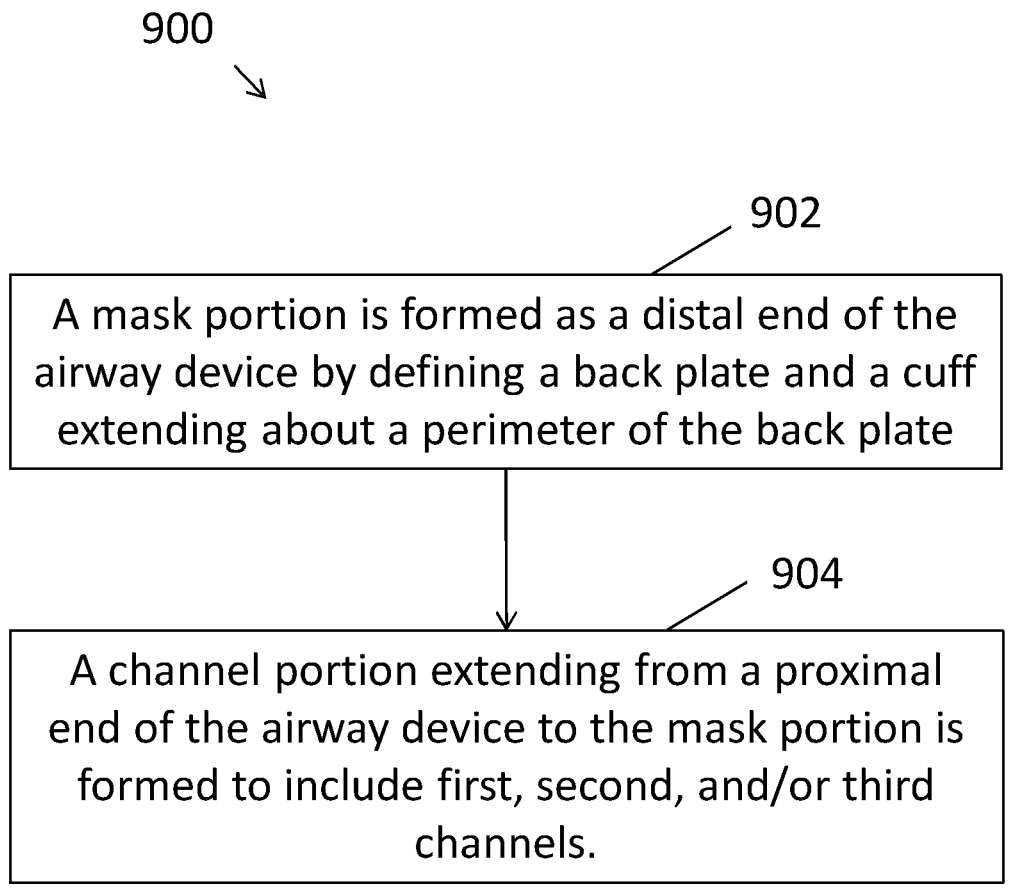
FIG. 11 is a flowchart illustrating an exemplary process for forming an embodiment of the airway device in accordance with embodiment of the present disclosure.

FIG. 11 is a flowchart illustrating an exemplary process 900 for forming an embodiment of the airway device 100. At step 902, a mask portion is formed as a distal end of the airway device for example by defining a back plate and a cuff extending about a perimeter of the back plate. The mask portion can be configured and dimensioned to be positioned in a hypopharyngeal area of a patient to cover and seal around a glottis of the patient with or without an inflatable or non-inflatable cuff. An ampulla and at least one sump can be formed in the mask portion, the at least one sump being formed in the back of the mask portion and being in fluid communication with the ampulla through a first port of the ampulla.

At step 904, a channel portion extending from a proximal end of the airway device to the mask portion is formed. Forming the channel portion can includes defining a first channel to extend from a first opening formed at the proximal end to a second opening formed at the back plate, defining a second channel to extend from a first opening of the second channel formed at the proximal end, and defining the second channel to extend alongside the first channel and to obliquely merge with the first channel proximate to the second opening of the first channel. The second channel forms an imaging channel. A third channel can be defined in the channel portion and a first opening of the third channel can be formed at the proximal end. The third channel can extend alongside the first and second channels from the proximal end to the ampulla. The third channel can be in fluid communication with the first and second ports of the ampulla. A groove can be formed in a side wall of the first channel proximate to the second opening where the second channel obliquely merges with the first channel. The groove tapers radially inward with respect to the first channel as the second channel merges with the first channel.

One or more kits can be formed including the components described herein. For example, a first kit can be formed that includes an embodiment of the airway device 100 and the left-sided BIT 60*a* or 160A. A second kit can be formed that includes an embodiment of the airway device 100 and the right-sided BIT 60*b* or 160B. A third kit can be formed that includes an embodiment of the airway device 100, the left-sided BIT 60*a* or 160A, and the right-sided BIT 60*b* or 160B. A fourth kit can be formed that includes an embodiment of the airway device 100 and the imaging tube 34. A fifth kit can be formed that includes an embodiment of the airway device 100 and one or more of the left-sided BIT 60*a* or 160A, the right-sided BIT 60*b* or 160B, and/or the imaging tube 34.

While principles of the present disclosure are described herein with reference to illustrative embodiments for particular applications, it should be understood that the disclosure is not limited thereto. Those having ordinary skill in the art and access to the teachings provided herein will recognize additional modifications, applications, embodiments, and substitution of equivalents all fall within the scope of the embodiments described herein. Accordingly, the invention is not to be considered as limited by the foregoing description.

What is claimed is:

1. A bronchial isolation tube comprising:
   an elongated non-collapsible tubular body extending from a proximal end to a distal end, the elongated non-collapsible tubular body configured and dimensioned to be inserted through an airway channel of a supraglottic airway device, crossing a glottis and a trachea, into a bronchus of the human;
   a first port disposed at the proximal end of the elongated non-collapsible tubular body;
   a distal opening disposed at the distal end of the elongated non-collapsible tubular body; and
   an inflatable member disposed on the distal end of the elongate non-collapsible tubular body to seal the bronchus,
   wherein the elongated non-collapsible tubular body has a portion with reduced diameters compared to a remainder of the elongated non-collapsible tubular body, the non-collapsible portion with the reduced diameters being positioned across the glottis of the human when the distal end of the elongated non-collapsible tubular body is positioned in the bronchus of the human.

2. The bronchial isolation tube of claim 1, wherein the elongated non-collapsible tubular body has a uniform thickness and firmness, the elongated non-collapsible including a tubular body, an upper section, a middle section, a lower section, and a distal section, wherein the middle section disposed between the upper and lower sections corresponds to the portion of the elongated non-collapsible tubular body with the reduced diameters.

3. The bronchial isolation tube of claim 2, wherein the diameters of the middle section are approximately a half millimeter to approximately one and a half millimeters less than the diameters of the remainder of the elongated non-collapsible tubular body.

4. The bronchial isolation tube of claim 2, wherein the elongated non-collapsible tubular body has a length measured along a central axis of the elongated non-collapsible tubular body from the proximal end to the distal end, wherein the middle section corresponds to ten to twenty percent of the length of the elongated non-collapsible tubular body.

5. The bronchial isolation tube of claim 2, wherein the elongated non-collapsible tubular body has a length measured along a central axis of the elongated non-collapsible tubular body from the proximal end to the distal end, and the middle section begins approximately two-hundred ten millimeters to approximately two-hundred fifty millimeters from the proximal end of the elongated non-collapsible tubular body.

6. The bronchial isolation tube of claim 2, wherein the elongated non-collapsible tubular body has a length measured along a central axis of the elongated non-collapsible tubular body from the proximal end to the distal end, and the middle section ends approximately two-hundred sixty millimeters to approximately three hundred millimeters from the proximal end of the elongated non-collapsible tubular body.

7. The bronchial isolation tube of claim 2, wherein the elongated non-collapsible tubular body has a length measured along a central axis of the elongated non-collapsible tubular body from the proximal end to the distal end, and wherein the upper section is four to six times longer than the middle section.

8. The bronchial isolation tube of claim 2, wherein the elongated non-collapsible tubular body has a length measured along a central axis of the elongated non-collapsible tubular body from the proximal end to the distal end, and wherein the lower section is approximately two to three times longer than the middle section.

9. The bronchial isolation tube of claim 2, wherein the elongated non-collapsible tubular body has a length measured along a central axis of the elongated non-collapsible tubular body from the proximal end to the distal end, and wherein the middle section has a length of approximately forty millimeters to approximately sixty millimeters.

10. The bronchial isolation tube of claim 2, wherein an outer diameter of the reduced diameters of the middle section is approximately ten to approximately twenty percent smaller than the outer diameter of the remainder of the elongated non-collapsible tubular body.

11. The bronchial isolation tube of claim 2, wherein the distal section includes the inflatable member disposed on the elongated non-collapsible tubular body in proximity to the distal end and a Murphy eye disposed in the elongated non-collapsible tubular body proximate to the distal end.

12. The bronchial isolation tube of claim 11, wherein the elongated non-collapsible tubular body extends linearly from the proximal end towards the distal section, and the distal section is biased so that the distal section extends at an angle relative to a remainder of the elongated non-collapsible tubular body.

13. The bronchial isolation tube of claim 12, wherein the distal section of the elongated non-collapsible tubular body extends at an angle of approximately twenty-five to approximately thirty-five degrees relative to the upper, middle, and lower sections of the elongated non-collapsible tubular body.

14. The bronchial isolation tube of claim 12, wherein the distal section of the elongated non-collapsible tubular body extends at an angle of approximately forty to approximately fifty degrees relative to the upper, middle, and lower sections of the elongated non-collapsible tubular body.

15. The bronchial isolation tube of claim 11, wherein the inflatable member is formed asymmetrically about the elongated non-collapsible tubular body and includes a short axis that extends between the Murphy eye and a visual indicator disposed proximally on the elongated non-collapsible tubular body relative to the Murphy eye.

16. The bronchial isolation tube of claim 15, wherein the inflatable member includes a long axis that extends between the visual indicator and the distal opening without covering the Murphy eye.

* * * * *